(12) United States Patent
Gross et al.

(10) Patent No.: US 11,129,981 B2
(45) Date of Patent: *Sep. 28, 2021

(54) DISC THERAPY

(71) Applicant: RAINBOW MEDICAL LTD., Herzliya (IL)

(72) Inventors: Yossi Gross, Moshav Mazor (IL); Gideon Fostick, Givat Shmuel (IL)

(73) Assignee: RAINBOW MEDICAL LTD., Herzliya (IL)

(*) Notice: Subject to any disclaimer, the term of this patent is extended or adjusted under 35 U.S.C. 154(b) by 22 days.

This patent is subject to a terminal disclaimer.

(21) Appl. No.: 16/695,936

(22) Filed: Nov. 26, 2019

(65) Prior Publication Data
US 2020/0164206 A1 May 28, 2020

Related U.S. Application Data

(63) Continuation of application No. 16/064,604, filed as application No. PCT/IL2016/051363 on Dec. 21,
(Continued)

(51) Int. Cl.
*A61N 1/20* (2006.01)
*A61N 1/32* (2006.01)
(Continued)

(52) U.S. Cl.
CPC ........... *A61N 1/205* (2013.01); *A61N 1/0551* (2013.01); *A61N 1/306* (2013.01); *A61N 1/325* (2013.01);
(Continued)

(58) Field of Classification Search
None
See application file for complete search history.

(56) References Cited

U.S. PATENT DOCUMENTS

| 4,044,774 A | 8/1977 | Corbin et al. |
| 4,503,863 A | 3/1985 | Katims |

(Continued)

FOREIGN PATENT DOCUMENTS

| WO | 94/05369 | 3/1994 |
| WO | 01/52931 | 7/2001 |

(Continued)

OTHER PUBLICATIONS

Karran September E et201 al., 1 "The Amyloid cascade hypothesis for AD," Nature Reviews Drug Discovery, vol. 10; 698-712.
(Continued)

*Primary Examiner* — Brian T Gedeon
(74) *Attorney, Agent, or Firm* — Sughrue Mion, PLLC

(57) ABSTRACT

Apparatus is provided that includes one or more intra-pulposus exposed electrode surfaces, and a support structure along which the one or more intra-pulposus exposed electrode surfaces are disposed. The support structure is configured to be implanted within a nucleus pulposus of an intervertebral disc of a subject, and to be shaped as a partial ring or a complete ring after implantation. The apparatus further includes one or more extra-pulposus exposed electrode surfaces, which are configured to be implanted outside the nucleus pulposus, in electrical communication with the disc. Control circuitry is provided, which is configured to: configure the intra-pulposus exposed electrode surfaces to be cathodes, and the one or more extra-pulposus exposed electrode surfaces to be one or more anodes, and drive the intra-pulposus exposed electrode surfaces and the one or more extra-pulposus exposed electrode surfaces to electroosmotically drive fluid into the nucleus pulposus. Other embodiments are also described.

16 Claims, 7 Drawing Sheets

Related U.S. Application Data 2016, now Pat. No. 10,518,085, which is a continuation of application No. 14/982,187, filed on Dec. 29, 2015, now Pat. No. 9,770,591.

(51) Int. Cl.
*A61N 1/30* (2006.01)
*A61N 1/05* (2006.01)
*A61N 1/36* (2006.01)
*A61N 1/375* (2006.01)
*A61N 1/372* (2006.01)

(52) U.S. Cl.
CPC .............. *A61N 1/326* (2013.01); *A61N 1/327* (2013.01); *A61N 1/36062* (2017.08); *A61N 1/36132* (2013.01); *A61N 1/37205* (2013.01); *A61N 1/37518* (2017.08)

(56) References Cited

U.S. PATENT DOCUMENTS

| | | |
|---|---|---|
| 5,088,977 A | 2/1992 | Sibalis |
| 5,121,754 A | 6/1992 | Mullett |
| 5,433,739 A | 7/1995 | Sluijter et al. |
| 5,529,574 A | 6/1996 | Frackelton |
| 5,587,297 A | 12/1996 | Jacobson et al. |
| 5,792,100 A | 8/1998 | Shantha |
| 5,911,223 A | 6/1999 | Weaver et al. |
| 5,919,163 A | 7/1999 | Glickman |
| 5,938,690 A | 8/1999 | Law et al. |
| 6,041,252 A | 3/2000 | Walker et al. |
| 6,146,380 A | 11/2000 | Racz et al. |
| 6,161,047 A | 12/2000 | King et al. |
| 6,360,750 B1 | 3/2002 | Gerber et al. |
| 6,506,408 B1 | 1/2003 | Palasis |
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |
| 6,907,295 B2 | 6/2005 | Gross et al. |
| 6,941,172 B2 | 9/2005 | Nachum |
| 6,997,941 B2 | 2/2006 | Sharkey et al. |
| 7,120,489 B2 | 10/2006 | Shalev et al. |
| 7,217,351 B2 | 5/2007 | Krumme |
| 7,223,227 B2 | 5/2007 | Pflueger |
| 7,270,659 B2 | 9/2007 | Ricart et al. |
| 7,398,121 B2 | 7/2008 | Matsumura et al. |
| 7,509,171 B2 | 3/2009 | DiMauro |
| 7,640,062 B2 | 12/2009 | Shalev |
| 7,831,306 B2 | 11/2010 | Finch et al. |
| 7,860,569 B2 | 12/2010 | Solberg et al. |
| 8,190,248 B2 | 5/2012 | Besio et al. |
| 8,457,761 B2 | 6/2013 | Wariar |
| 8,577,469 B2 | 11/2013 | Gross |
| 8,676,348 B2 | 3/2014 | Gross |
| 9,616,221 B2 | 4/2017 | Gross |
| 9,724,513 B2 | 8/2017 | Lane et al. |
| 9,770,591 B2 | 9/2017 | Gross |
| 9,950,156 B2 | 4/2018 | Gross et al. |
| 10,518,085 B2 | 12/2019 | Gross |
| 10,765,527 B2 | 9/2020 | Chin et al. |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0083002 A1 | 4/2004 | Belef et al. |
| 2004/0116977 A1 | 6/2004 | Finch et al. |
| 2004/0186576 A1 | 9/2004 | Biscup et al. |
| 2004/0210209 A1 | 10/2004 | Yeung et al. |
| 2004/0253304 A1 | 12/2004 | Gross et al. |
| 2004/0267240 A1 | 12/2004 | Gross et al. |
| 2005/0010205 A1 | 1/2005 | Hovda et al. |
| 2005/0021104 A1 | 1/2005 | DiLorenzo |
| 2005/0058701 A1 | 3/2005 | Gross et al. |
| 2005/0119650 A1 | 6/2005 | Sanders et al. |
| 2005/0159790 A1 | 7/2005 | Shalev |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0276844 A1 | 12/2006 | Alon et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0213700 A1 | 9/2007 | Davison et al. |
| 2007/0276201 A1 | 11/2007 | Lee et al. |
| 2008/0009927 A1 | 1/2008 | Vilims |
| 2008/0063703 A1 | 3/2008 | Gross et al. |
| 2008/0119907 A1 | 5/2008 | Stahmann |
| 2008/0177392 A1 | 7/2008 | Williams et al. |
| 2008/0188837 A1 | 8/2008 | Belsky et al. |
| 2008/0260542 A1 | 10/2008 | Nishikawa et al. |
| 2008/0275430 A1 | 11/2008 | Belsky et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0216113 A1 | 8/2009 | Meier et al. |
| 2009/0312816 A1 | 12/2009 | Gross |
| 2010/0057204 A1 | 3/2010 | Kadaba et al. |
| 2010/0100185 A1 | 4/2010 | Trieu et al. |
| 2010/0131067 A1 | 5/2010 | Metcalf, Jr. et al. |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0125158 A1 | 5/2011 | Diwan et al. |
| 2011/0160638 A1 | 6/2011 | Mauge et al. |
| 2011/0160797 A1 | 6/2011 | Makous et al. |
| 2012/0203307 A1 | 8/2012 | Schroeppel et al. |
| 2013/0066392 A1 | 3/2013 | Simon et al. |
| 2013/0102952 A1 | 4/2013 | Gross |
| 2013/0166006 A1 | 6/2013 | Williams |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0119898 A1 | 4/2015 | Desalles et al. |
| 2016/0331970 A1 | 11/2016 | Lozano |
| 2017/0007823 A1 | 1/2017 | Gross |
| 2017/0120053 A1 | 5/2017 | Fostick et al. |
| 2017/0182317 A1 | 6/2017 | Gross et al. |
| 2018/0071523 A1 | 3/2018 | Gross et al. |

FOREIGN PATENT DOCUMENTS

| | | |
|---|---|---|
| WO | 01/85027 | 11/2001 |
| WO | 2001/085094 | 11/2001 |
| WO | 2004/066903 | 8/2004 |
| WO | 2005/105053 | 11/2005 |
| WO | 2006/064502 | 6/2006 |
| WO | 2006/064503 | 6/2006 |
| WO | 2006/090397 | 8/2006 |
| WO | 2006/123346 | 11/2006 |
| WO | 2008/007369 | 1/2008 |
| WO | 2008/084477 | 7/2008 |
| WO | 2017/006327 | 1/2017 |
| WO | 2017/072769 | 5/2017 |

OTHER PUBLICATIONS

De La Torre JC, "Vascular Basis of Alzheimer's Pathogensis," Ann NY Acad Sci. 977:196-215 (Nov. 2002).
Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.
Brief PubMed search for metal ions in Alzheimers.

(56) References Cited

OTHER PUBLICATIONS

An Office Action dated Sep. 27, 2016, which issued during the prosecution of U.S. Appl. No. 14/926,705.
An International Search Report and a Written Opinion both dated Aug. 7, 2008, which issued during the prosecution of Applicant's PCT/IL2007/000865.
An Office Action dated Mar. 29, 2013, which issued during the prosecution of U.S. Appl. No. 12/373,306.
An Office Action dated Oct. 31, 2011, which issued during the prosecution of U.S. Appl. No. 12/373,306.
An Office Action dated Oct. 1, 2012, which issued during the prosecution of U.S. Appl. No. 12/373,306.
Notice of Allowance dated Jul. 24, 2013, which issued during the prosecution of U.S. Appl. No. 12/373,306.
An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann IM et al., "In-vitro evaluation of a drainage catheter with integrated bioimpedance electrodes to determine ventricular size," Biomed Tech 2013; 58 (Suppl. 1) Sep. 2013 (2 pages total).
An Office Action dated Aug. 31, 2015, which issued during the prosecution of U.S. Appl. No. 13/872,794.
An Applicant Initiated Interview Summary dated Dec. 14, 2015, which issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
U.S. Appl. No. 60/830,717, filed Jul. 12, 2006.
Vernengo J, "Injectable Bioadhesive Hydrogels for Nucleus Pulposus Replacement and Repair of the Damaged Intervertebral Disc: A Thesis," Drexel University (Jan. 2007).
Cheung KMC et al., "Intervertebral disc regeneration by use of autologous mesenchymal stem cells, an experimental model in rabbits, " Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
Urban JPG et al., "The nucleus of the intervertebral disc from development to degeneration," American Zoologist 40(1): 53-61 (2000).
Restriction Requirement dated Sep. 12, 2011, which issued during the prosecution of U.S. Appl. No. 12/373,306.
An International Preliminary Report on Patentability dated Apr. 7, 2009, which issued during the prosecution of Applicant's PCT/IL2007/000865.
An International Preliminary Report on Patentability dated Dec. 22, 2009, which issued during the prosecution of Applicant's PCT/IL2008/000038.
An International Search Report and a Written Opinion both dated Sep. 2, 2008, which issued during the prosecution of Applicant's PCT/IL2008/000038.
An Office Action dated Jan. 16, 2015, which issued during the prosecution of U.S. Appl. No. 13/872,794.
Loutzenhiser, "Membrane Potential measurements in renal afferent and efferent arterioles: actions of Angiotensin II", AJP-Renal Physiol Aug. 1, 1997 vol. 273 No. 2 F307-F314.
Iatridis JC et al., "Influence of fixed charge density magnitude and distribution on the intervertebral disc: applications of a poroelastic and chemical electric (PEACE) model," J Biomech Eng. 125(1):12-24 (Feb. 2003).
"Implanting ultrathin electrodes in soft tissue" https://www.youtube.com/watch?v=FaBYQ68JIM8&spfreload=10, Published on Oct. 10, 2014 (excerpts from video).
Service RF, "Electric fields deliver drugs into tumors,"http://news.sciencemag.org, Feb. 4, 2015.
Dao-Sheng Liu et al., "Activation of Na+ and K+ Pumping Modes of (Na,K)-ATPase by an Oscillating Electric Field," The Journal of Biological Chemistry, vol. 265. No. 13, May 5, 1990.(pp. 7260-7267).
An International Search Reportt and a Written Opinion both dated Jan. 26, 2017, which issued during the prosecution of Applicant's PCT/IL2016/051161.
An International Search Report and a Written Opinion both dated Mar. 10, 2017, which issued during the prosecution of Applicant's PCT/IL2016/051363.
An Office Action dated May 26, 2017, which issued during the prosecution of U.S. Appl. No. 15/453,290.
Notice of Allowance dated Jul. 24, 2017, which issued during the prosecution of U.S. Appl. No. 14/982,187.
Notice of Allowance dated Dec. 13, 2017, which issued during the prosecution of U.S. Appl. No. 15/263,910.
Corrected Notice of Allowability dated Jan. 3, 2018, which issued during the prosecution of U.S. Appl. No. 15/263,910.
An Office Action dated Apr. 25, 2018, which issued during the prosecution of U.S. Appl. No. 15/637,330.
An Invitation to pay additional fees dated Dec. 12, 2017, which issued during the prosecution of Applicant's PCT/IL2017/051032.
An International Search Report and a Written Opinion both dated Feb. 12, 2018, which issued during the prosecution of Applicant's PCT/IL2017/051032.
A Non-Final Office Action issued in U.S. Appl. No. 16/558,987, dated Feb. 16, 2021.

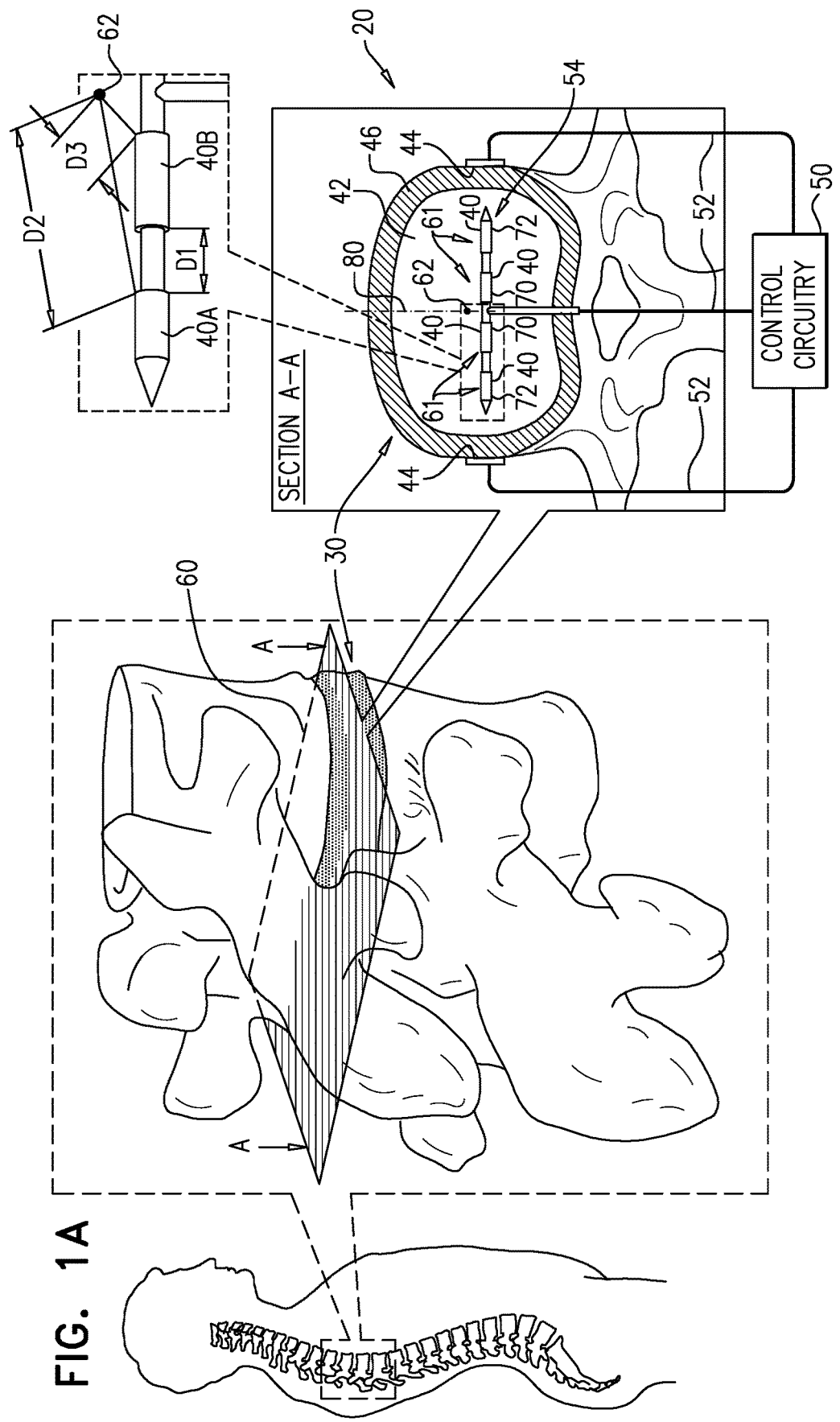

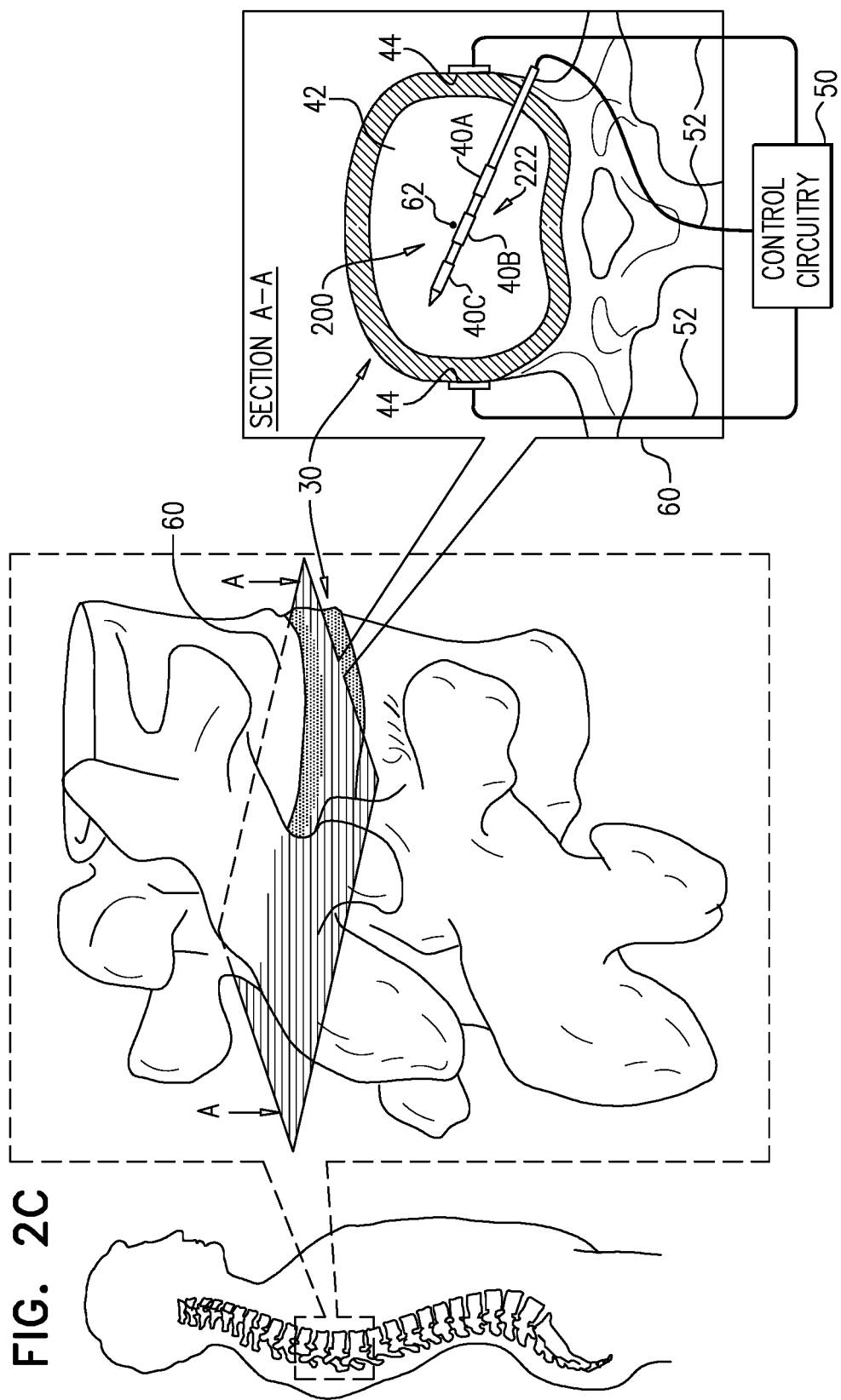

12
DISC THERAPY

CROSS-REFERENCE TO RELATED APPLICATIONS

The present application is a continuation of U.S. application Ser. No. 16/064,604, filed Jun. 21, 2018, now U.S. Pat. No. 10,518,085, which is the U.S. national stage of International Application PCT/IL2016/051363, filed Dec. 21, 2016, which is a continuation of U.S. application Ser. No. 14/982,187, filed Dec. 29, 2015, now U.S. Pat. No. 9,770,591, which is assigned to the assignee of the present application and is incorporated herein by reference.

FIELD OF THE APPLICATION

The present invention relates generally to therapeutic electrical techniques, and specifically to apparatus and methods for application of therapeutic electrical energy to the spinal column.

BACKGROUND OF THE APPLICATION

The intervertebral discs form cartilaginous joints between the end plates of vertebrae to provide shock absorption. The discs include two main regions: the nucleus pulposus, which is an inner, soft and highly hydrated structure, and the annulus fibrosus, which is a strong structure including lamellae (concentric sheets of collagen fibers), which surrounds the nucleus. The three major constituents of the discs are water, fibrillar collagens, and aggrecan. The proportion of these components varies across the disc, with the nucleus having a higher concentration of aggrecan and water and a lower collagen content than other regions of the disc. The loss of water content, particularly in the nucleus pulposus, is associated with disc degeneration, and with a decrease in disc height and abnormal loading of other spinal structures.

U.S. Pat. No. 8,577,469 to Gross, which is assigned to the assignee of the present application and is incorporated herein by reference, describes apparatus for treating an intervertebral disc of a subject. The apparatus includes a first electrode, configured to be inserted into a nucleus pulposus of the disc, and a second electrode, configured to be placed outside of the nucleus pulposus, in a vicinity of the nucleus pulposus. A control unit is configured to drive a current between the first and second electrodes, and to configure the current to electroosmotically drive fluid between inside and outside the nucleus pulposus. Other embodiments are also described U.S. Patent Application Publication 2005/0277996 to Podhajsky describes a method for reducing intervertebral pressure, including providing an electrode, having proximal and distal ends, and a generator, which is operatively connected to the proximal end of the electrode, and is configured to supply radio frequency current thereto. The method also includes inserting at least a portion of the distal end of the electrode into the nucleus pulposus of an intervertebral disc and activating the generator to heat the nucleus pulposus. The electrode may be inserted into the intervertebral disc through its first lateral side and/or its second lateral side, and may be substantially parallel to the major or minor axis of the nucleus pulposus.

SUMMARY OF THE APPLICATION

In some applications of the present invention, a method of treating an intervertebral disc of comprises implanting, within a nucleus pulposus of the disc, at least three intra-pulposus exposed electrode surfaces at different respective locations, and implanting one or more extra-pulposus exposed electrode surfaces outside the nucleus pulposus, in electrical communication with the disc. Control circuitry is activated to drive the intra-pulposus exposed electrode surfaces and the one or more extra-pulposus exposed electrode surfaces to electroosmotically drive fluid between inside and outside the nucleus pulposus.

In some applications of the present invention, the control circuitry is activated to increase pressure in the disc by electroosmotically driving the fluid into the nucleus pulposus. For some applications, the control circuitry is activated to configure the intra-pulposus exposed electrode surfaces to be cathodes, and the one or more extra-pulposus exposed electrode surfaces to be one or more anodes. For some applications, the control circuitry is activated to configure the cathodes to be at different respective negative potentials. For some applications, the control circuitry is activated to set respective magnitudes of the negative potentials at the cathodes, with respect to outside the nucleus pulposus, to be inversely related to respective distances between the geometric center and the cathodes. In other words, the negative potentials are greater closer to the geometric center. This approach is based on the inventors' realization that the potential distribution within in a disc is not homogeneous, and in a pathological disc the negative potential near the geometric center of the disc is reduced (i.e., closer to zero) as compared to a healthy disc. The application of differing negative potentials at different locations within the disc corrects this abnormal negative potential distribution within the pathological disc In some applications of the present invention, a method comprises systemically administering a drug to a blood circulation of a subject, and activating control circuitry to apply, using one or more implanted electrodes, a current that drives the administered drug from the blood circulation into tissue of the subject, including at at least one point in time at which the drug has a concentration in the blood circulation equal to at least 75% of a maximum concentration of the drug in the blood circulation.

There is therefore provided, in accordance with an inventive concept 1 of the present invention, a method of treating an intervertebral disc of a subject, including:

implanting, within a nucleus pulposus of the disc, at least three intra-pulposus exposed electrode surfaces at different respective locations;

implanting one or more extra-pulposus exposed electrode surfaces outside the nucleus pulposus, in electrical communication with the disc; and activating control circuitry to:
configure the intra-pulposus exposed electrode surfaces to be cathodes, and the one or more extra-pulposus exposed electrode surfaces to be one or more anodes, and drive the intra-pulposus exposed electrode surfaces and the one or more extra-pulposus exposed electrode surfaces to electroosmotically drive fluid into the nucleus pulposus to increase pressure in the disc.

Inventive concept 2. The method according to inventive concept 1, wherein implanting the intra-pulposus exposed electrode surfaces includes implanting the intra-pulposus exposed electrode surfaces such that if the intra-pulposus exposed electrode surfaces were to be projected onto a transverse plane of the disc, the intra-pulposus exposed electrode surfaces would be at different respective projected locations in the transverse plane.

Inventive concept 3. The method according to inventive concept 2, wherein implanting the intra-pulposus exposed electrode surfaces includes implanting the intra-pulposus exposed electrode surfaces such that if the intra-pulposus exposed electrode surfaces were to be projected onto the transverse plane of the disc, each of the intra-pulposus exposed electrode surfaces would be at least 2 mm from a closest another one of the intra-pulposus exposed electrode surfaces.

Inventive concept 4. The method according to inventive concept 2, wherein implanting the intra-pulposus exposed electrode surfaces includes implanting the intra-pulposus exposed electrode surfaces such that if the intra-pulposus exposed electrode surfaces were to be projected onto the transverse plane of the disc, at least two of the intra-pulposus exposed electrode surfaces would be disposed at respective different distances from a geometric center of the disc in the transverse plane.

Inventive concept 5. The method according to inventive concept 4, wherein implanting the intra-pulposus exposed electrode surfaces includes implanting the intra-pulposus exposed electrode surfaces such that if the intra-pulposus exposed electrode surfaces were to be projected onto the transverse plane of the disc, at least three of the intra-pulposus exposed electrode surfaces would be disposed at respective different distances from the geometric center of the disc in the transverse plane.

Inventive concept 6. The method according to inventive concept 4, wherein implanting the intra-pulposus exposed electrode surfaces includes implanting the intra-pulposus exposed electrode surfaces such that if the intra-pulposus exposed electrode surfaces were to be projected onto the transverse plane of the disc, at least one of the distances would be at least 2 mm greater than another one of the distances.

Inventive concept 7. The method according to inventive concept 4, wherein implanting the intra-pulposus exposed electrode surfaces includes implanting the intra-pulposus exposed electrode surfaces such that if the intra-pulposus exposed electrode surfaces were to be projected onto the transverse plane of the disc, at least (a) a first one of the distances would be at least 2 mm greater than a second one of the distances, and (b) a third one of one of the distances would be at least 2 mm greater than the second one of the distances.

Inventive concept 8. The method according to inventive concept 1, wherein implanting the intra-pulposus exposed electrode surfaces includes implanting the intra-pulposus exposed electrode surfaces such that if the intra-pulposus exposed electrode surfaces were to be projected onto a transverse plane of the disc, at least one of the intra-pulposus exposed electrode surfaces would be disposed at a distance of no more than 10 mm from a geometric center of the disc in the transverse plane.

Inventive concept 9. The method according to inventive concept 1, wherein activating the control circuitry to drive the intra-pulposus exposed electrode surfaces and the one or more extra-pulposus exposed electrode surfaces to electroosmotically drive the fluid into the nucleus pulposus includes activating the control circuitry to apply:
(a) a first voltage between at least a first one of the intra-pulposus exposed electrode surfaces and at least one of the one or more extra-pulposus exposed electrode surfaces, and
(b) a second voltage between at least a second one of the intra-pulposus exposed electrode surfaces and at least one of the one or more extra-pulposus exposed electrode surfaces, the second voltage different from the first voltage.

Inventive concept 10. The method according to inventive concept 9, wherein activating the control circuitry to drive the intra-pulposus exposed electrode surfaces and the one or more extra-pulposus exposed electrode surfaces to electroosmotically drive the fluid into the nucleus pulposus includes activating the control circuitry to apply a third voltage between at least a third one of the intra-pulposus exposed electrode surfaces and at least one of the one or more extra-pulposus exposed electrode surfaces, the third voltage different from at least one of the first and the second voltages.

Inventive concept 11. The method according to inventive concept 10, wherein the third voltage is different from both the first and the second voltages.

Inventive concept 12. The method according to inventive concept 1, wherein implanting the at least three intra-pulposus exposed electrode surfaces includes implanting, within the nucleus pulposus, at least five intra-pulposus exposed electrode surfaces at different respective locations.

Inventive concept 13. The method according to inventive concept 12, wherein implanting the at least five intra-pulposus exposed electrode surfaces includes implanting the at least five intra-pulposus exposed electrode surfaces such that if the intra-pulposus exposed electrode surfaces were to be projected onto a transverse plane of the disc, the intra-pulposus exposed electrode surfaces would be at different respective projected locations in the transverse plane.

Inventive concept 14. The method according to inventive concept 1, wherein activating the control circuitry includes activating the control circuitry to configure the cathodes to be at different respective negative potentials.

Inventive concept 15. The method according to inventive concept 14,
wherein if the cathodes were to be projected onto a transverse plane of the disc, one or more of the cathodes would be one or more respective closest cathodes to a geometric center of the disc in the transverse plane of the disc, and
wherein activating the control circuitry includes activating the control circuitry to set respective magnitudes of the negative potentials at the one or more closest cathodes to be at least 30 mV with respect to outside the nucleus pulposus.

Inventive concept 16. The method according to inventive concept 15, wherein activating the control circuitry includes activating the control circuitry to set the respective magnitudes of the negative potentials at the one or more closest cathodes to be at least 40 mV with respect to outside the nucleus pulposus.

Inventive concept 17. The method according to inventive concept 15,
wherein if the cathodes were to be projected onto the transverse plane of the disc, one or more of the cathodes would be one or more respective farthest cathodes from the geometric center of the disc in the transverse plane of the disc, and
wherein activating the control circuitry includes activating the control circuitry to set respective magnitudes of the negative potentials at the one or more farthest cathodes to be no more than 20 mV with respect to outside the nucleus pulposus.

Inventive concept 18. The method according to inventive concept 14, wherein implanting the intra-pulposus exposed electrode surfaces includes implanting the intra-pulposus exposed electrode surfaces such that if the intra-pulposus exposed electrode surfaces were to be projected onto a transverse plane of the disc, the intra-pulposus exposed electrode surfaces would be disposed at respective distances from a geometric center of the disc in the transverse plane, and wherein activating the control circuitry includes activating the control circuitry to set respective magnitudes of the negative potentials at the cathodes, with respect to outside the nucleus pulposus, to be inversely related to the respective distances between the geometric center and the cathodes.

Inventive concept 19. The method according to inventive concept 18, wherein if the cathodes were to be projected onto a transverse plane of the disc, one or more of the cathodes would be one or more respective closest cathodes to a geometric center of the disc in the transverse plane of the disc, and one or more of the cathodes would be one or more respective farthest cathodes to the geometric center of the disc in the transverse plane of the disc, and wherein activating the control circuitry includes activating the control circuitry to set respective magnitudes of the negative potentials at the one or more closest cathodes, with respect to outside the nucleus pulposus, to be greater than respective magnitudes of the negative potential at the one or more farthest cathodes, with respect to outside the nucleus pulposus.

Inventive concept 20. The method according to inventive concept 19, wherein activating the control circuitry includes activating the control circuitry to set the respective magnitudes of the negative potentials at the one or more closest cathodes, with respect to outside the nucleus pulposus, to be at least 20 mV greater than the respective magnitudes of the negative potentials at the one or more farthest cathodes, with respect to outside the nucleus pulposus.

Inventive concept 21. The method according to inventive concept 20, wherein activating the control circuitry includes activating the control circuitry to set the respective magnitudes of the negative potentials at the one or more closest cathodes, with respect to outside the nucleus pulposus, to be at least 30 mV greater than the respective magnitudes of the negative potentials at the one or more farthest cathodes, with respect to outside the nucleus pulposus.

Inventive concept 22. The method according to inventive concept 1, wherein implanting the intra-pulposus exposed electrode surfaces includes implanting the intra-pulposus exposed electrode surfaces symmetrically about a sagittal plane of the disc.

Inventive concept 23. The method according to inventive concept 1, wherein implanting the intra-pulposus exposed electrode surfaces includes implanting at least one intra-pulposus electrode, which includes:
 at least two of the intra-pulposus exposed electrode surfaces; and
 a support structure along which the at least two of the intra-pulposus exposed electrode surfaces are disposed, such that the support structure is shaped as a partial ring or a complete ring after the implanting.

Inventive concept 24. The method according to inventive concept 23,
 wherein the disc defines a geometric center line segment perpendicular to a transverse plane of the disc, and wherein implanting the at least one intra-pulposus electrode includes implanting the at least one intra-pulposus electrode such that the support structure surrounds at least 180 degrees of the geometric center line segment.

Inventive concept 25. The method according to inventive concept 24, wherein implanting the at least one intra-pulposus electrode includes implanting the at least one intra-pulposus electrode such that the support structure surrounds at least 270 degrees of the geometric center line segment.

Inventive concept 26. The method according to inventive concept 23, wherein implanting the at least one intra-pulposus electrode includes implanting the at least one intra-pulposus electrode such that the support structure is shaped as the complete ring that surrounds an area of at least 1 cm2.

Inventive concept 27. The method according to inventive concept 23, wherein implanting the at least one intra-pulposus electrode includes implanting the at least one intra-pulposus electrode such that the support structure is shaped as the complete ring that surrounds an area equal to at least 15% of a greatest area of the nucleus pulposus measured in a transverse plane of the disc.

Inventive concept 28. The method according to inventive concept 23, wherein implanting the at least one intra-pulposus electrode includes implanting the at least one intra-pulposus electrode such that the support structure is shaped as the partial ring that surrounds an area of at least 1 cm2.

Inventive concept 29. The method according to inventive concept 23, wherein implanting the at least one intra-pulposus electrode includes implanting the at least one intra-pulposus electrode such that the support structure is shaped as the partial ring that surrounds an area equal to at least 15% of a greatest area of the nucleus pulposus measured in a transverse plane of the disc.

Inventive concept 30. The method according to inventive concept 23, wherein the at least one intra-pulposus electrode includes a partially insulated wire, which serves as the support structure, and wherein non-insulated portions of the wire serve as respective ones of the intra-pulposus exposed electrode surfaces.

Inventive concept 31. The method according to inventive concept 1, wherein implanting the intra-pulposus exposed electrode surfaces includes implanting at least one intra-pulposus electrode, which includes:
 at least two of the intra-pulposus exposed electrode surfaces; and
 a support structure along which the at least two of the intra-pulposus exposed electrode surfaces are disposed, such that the support structure remains straight during and after the implanting.

Inventive concept 32. The method according to inventive concept 31, wherein the at least one intra-pulposus electrode includes a partially insulated wire, which serves as the support structure, and wherein non-insulated portions of the wire serve as respective ones of the intra-pulposus exposed electrode surfaces.

Inventive concept 33. The method according to inventive concept 31,
 wherein the at least two of the intra-pulposus exposed electrode surfaces include first, second, and third intra-pulposus exposed electrode surfaces disposed along the support structure, with the second longitudinally between the first and the third intra-pulposus exposed electrode surfaces, and wherein activating the control circuitry includes activating the control circuitry to configure the first, the second, and the third intra-pulposus exposed electrode surfaces to be at respective different potentials, the potential at the second intra-pulposus exposed electrode surface (a) greater than the potential at the first intra-pulposus exposed electrode surface, and (b) greater than the potential at the third intra-pulposus exposed electrode surface.

Inventive concept 34. The method according to inventive concept 33, wherein implanting the intra-pulposus exposed electrode surfaces includes implanting the intra-pulposus exposed electrode surfaces such that if the intra-pulposus exposed electrode surfaces were to be projected onto a transverse plane of the disc:
the first, the second, and the third intra-pulposus exposed electrode surfaces would be disposed at respective first, second, and third distances from a geometric center of the disc in the transverse plane, and
the second distance would be (a) less than the first distance, and (b) less than the third distance.

Inventive concept 35. The method according to inventive concept 1, wherein implanting the intra-pulposus exposed electrode surfaces includes implanting at least one intra-pulposus electrode, which includes:
at least two of the intra-pulposus exposed electrode surfaces; and
a support structure, which includes a plurality of spines that respectively include one or more of the intra-pulposus exposed electrode surfaces.

Inventive concept 36. The method according to inventive concept 35, wherein the support structure further includes a backbone, from which the spines extend.

Inventive concept 37. The method according to inventive concept 35, wherein the support structure includes a partially insulated wire, and wherein non-insulated portions of the wire serve as respective ones of the intra-pulposus exposed electrode surfaces.

Inventive concept 38. The method according to inventive concept 1, wherein implanting the one or more extra-pulposus exposed electrode surfaces includes implanting the one or more extra-pulposus exposed electrode surfaces within 1 mm of the nucleus pulposus of the disc.

Inventive concept 39. The method according to inventive concept 1, wherein implanting the one or more extra-pulposus exposed electrode surfaces includes implanting the one or more extra-pulposus exposed electrode surfaces between 1 and 15 mm from the nucleus pulposus of the disc.

Inventive concept 40. The method according to inventive concept 1, wherein implanting the one or more extra-pulposus exposed electrode surfaces includes implanting the one or more extra-pulposus exposed electrode surfaces within 1 mm of an external surface of an annulus fibrosus of the disc.

Inventive concept 41. The method according to inventive concept 1, wherein implanting the one or more extra-pulposus exposed electrode surfaces includes implanting the one or more extra-pulposus exposed electrode surfaces at least partially within an annulus fibrosus of the disc.

Inventive concept 42. The method according to inventive concept 1, wherein implanting the one or more extra-pulposus exposed electrode surfaces includes implanting the one or more extra-pulposus exposed electrode surfaces at an average distance from the nucleus pulposus of the disc that is inversely related to a number of the one or more extra-pulposus exposed electrode surfaces being implanted.

Inventive concept 43. The method according to inventive concept 1, wherein implanting the one or more extra-pulposus exposed electrode surfaces includes implanting the one or more extra-pulposus exposed electrode surfaces such that a product of (a) a number of the one or more extra-pulposus exposed electrode surfaces times (b) an average distance in centimeters of the one or more extra-pulposus exposed electrode surfaces from the nucleus pulposus equals between 4 and 15.

Inventive concept 44. The method according to inventive concept 1, wherein activating the control circuitry includes activating the control circuitry to:
drive the intra-pulposus exposed electrode surfaces and the one or more extra-pulposus exposed electrode surfaces to electroosmotically drive the fluid into the nucleus pulposus during a plurality of discrete activation periods alternating with non-activation periods, and
ramp a strength of currents applied between the intra-pulposus exposed electrode surfaces and the one or more extra-pulposus exposed electrode surfaces at a beginning of at least one of the activation periods such that the strength reaches a maximum value no earlier than 10 minutes after the beginning of the period.

Inventive concept 45. The method according to inventive concept 44, wherein activating the control circuitry includes activating the control circuitry to set a length of at least one of the non-activation periods to be at least 30 minutes.

Inventive concept 46. The method according to inventive concept 1, wherein activating the control circuitry includes activating the control circuitry to drive the intra-pulposus exposed electrode surfaces and the one or more extra-pulposus exposed electrode surfaces to electroosmotically drive the fluid into the nucleus pulposus based on a circadian cycle of the subject.

Inventive concept 47. The method according to inventive concept 1, further including replacing the nucleus pulposus with an artificial substitute material before implanting the intra-pulposus exposed electrode surfaces.

There is further provided, in accordance with an inventive concept 48 of the present invention, a method of treating an intervertebral disc of a subject, including:
implanting, within a nucleus pulposus of the disc, a support structure along which one or more intra-pulposus exposed electrode surfaces are disposed, such that the support structure is shaped as a partial ring or a complete ring after the implanting;
implanting one or more extra-pulposus exposed electrode surfaces outside the nucleus pulposus, in electrical communication with the disc; and
activating control circuitry to:
configure the intra-pulposus exposed electrode surfaces to be cathodes, and the one or more extra-pulposus exposed electrode surfaces to be one or more anodes, and,
drive the intra-pulposus exposed electrode surfaces and the one or more extra-pulposus exposed electrode surfaces to electroosmotically drive fluid into the nucleus pulposus to increase pressure in the disc.

Inventive concept 49. The method according to inventive concept 48, wherein the support structure includes a wire, and wherein the one or more intra-pulposus exposed electrode surfaces are defined by one or more non-insulated portions of the wire.

Inventive concept 50. The method according to inventive concept 49, wherein the wire has a diameter of no more than 200 microns.

Inventive concept 51. The method according to inventive concept 48,
wherein the disc defines a geometric center line segment perpendicular to a transverse plane of the disc, and
wherein implanting the support structure includes implanting the support structure such that the support structure surrounds at least 180 degrees of the geometric center line segment.

Inventive concept 52. The method according to inventive concept 51, wherein implanting the support structure includes implanting the support structure such that the support structure surrounds at least 270 degrees of the geometric center line segment.

Inventive concept 53. The method according to inventive concept 48, wherein implanting the support structure includes implanting the support structure such that the support structure is shaped as the complete ring that surrounds an area of at least 1 cm2.

Inventive concept 54. The method according to inventive concept 48, wherein implanting the support structure includes implanting the support structure such that the support structure is shaped as the complete ring that surrounds an area equal to at least 15% of a greatest area of the nucleus pulposus measured in a transverse plane of the disc.

Inventive concept 55. The method according to inventive concept 48, wherein implanting the support structure includes implanting the support structure such that the support structure is shaped as the partial ring that surrounds an area of at least 1 cm2.

Inventive concept 56. The method according to inventive concept 48, wherein implanting the support structure includes implanting the support structure such that the support structure is shaped as the partial ring that surrounds an area equal to at least 15% of a greatest area of the nucleus pulposus measured in a transverse plane of the disc.

There is still further provided, in accordance with an inventive concept 57 of the present invention, apparatus for treating an intervertebral disc of a subject, the apparatus including:
at least three intra-pulposus exposed electrode surfaces, which are configured to be implanted within a nucleus pulposus of the disc, at different respective locations;
one or more extra-pulposus exposed electrode surfaces, which are configured to be implanted outside the nucleus pulposus, in electrical communication with the disc; and
control circuitry, which is configured to:
configure the intra-pulposus exposed electrode surfaces to be cathodes, and the one or more extra-pulposus exposed electrode surfaces to be one or more anodes, and
drive the intra-pulposus exposed electrode surfaces and the one or more extra-pulposus exposed electrode surfaces to electroosmotically drive fluid into the nucleus pulposus to increase pressure in the disc.

Inventive concept 58. The apparatus according to inventive concept 57, wherein the apparatus includes at least five intra-pulposus exposed electrode surfaces, which are configured to be implanted implanting within the nucleus pulposus, at different respective locations.

Inventive concept 59. The apparatus according to inventive concept 57, wherein the control circuitry is configured to configure the cathodes to be at different respective negative potentials.

Inventive concept 60. The apparatus according to inventive concept 57, wherein the control circuitry is configured to:
drive the intra-pulposus exposed electrode surfaces and the one or more extra-pulposus exposed electrode surfaces to electroosmotically drive the fluid into the nucleus pulposus during a plurality of discrete activation periods alternating with non-activation periods, and
ramp a strength of currents applied between the intra-pulposus exposed electrode surfaces and the one or more extra-pulposus exposed electrode surfaces at a beginning of at least one of the activation periods such that the strength reaches a maximum value no earlier than 10 minutes after the beginning of the period.

Inventive concept 61. The apparatus according to inventive concept 60, wherein the control circuitry is configured to set a length of at least one of the non-activation periods to be at least 30 minutes.

Inventive concept 62. The apparatus according to inventive concept 57, wherein the control circuitry is configured to drive the intra-pulposus exposed electrode surfaces and the one or more extra-pulposus exposed electrode surfaces to electroosmotically drive the fluid into the nucleus pulposus based on a circadian cycle of the subject.

Inventive concept 63. The apparatus according to any one of inventive concepts 57-62, wherein the control circuitry is configured to drive the intra-pulposus exposed electrode surfaces and the one or more extra-pulposus exposed electrode surfaces to electroosmotically drive the fluid into the nucleus pulposus by applying:
(a) a first voltage between at least a first one of the intra-pulposus exposed electrode surfaces and at least one of the one or more extra-pulposus exposed electrode surfaces, and
(b) a second voltage between at least a second one of the intra-pulposus exposed electrode surfaces and at least one of the one or more extra-pulposus exposed electrode surfaces, the second voltage different from the first voltage.

Inventive concept 64. The apparatus according to inventive concept 63, wherein the control circuitry is configured to drive the intra-pulposus exposed electrode surfaces and the one or more extra-pulposus exposed electrode surfaces to electroosmotically drive the fluid into the nucleus pulposus by applying a third voltage between at least a third one of the intra-pulposus exposed electrode surfaces and at least one of the one or more extra-pulposus exposed electrode surfaces, the third voltage different from at least one of the first and the second voltages.

Inventive concept 65. The apparatus according to inventive concept 64, wherein the third voltage is different from both the first and the second voltages.

Inventive concept 66. The apparatus according to any one of inventive concepts 57-62, wherein the apparatus includes at least one intra-pulposus electrode, which includes:
at least two of the intra-pulposus exposed electrode surfaces; and
a support structure along which the at least two of the intra-pulposus exposed electrode surfaces are disposed, wherein the support structure is configured to be shaped as a partial ring or a complete ring after implantation.

Inventive concept 67. The apparatus according to inventive concept 66, wherein the support structure is configured to be shaped as the complete ring that surrounds an area of at least 1 cm2.

Inventive concept 68. The apparatus according to inventive concept 66, wherein the support structure is configured to be shaped as the partial ring that surrounds an area of at least 1 cm2.

Inventive concept 69. The apparatus according to inventive concept 66, wherein the at least one intra-pulposus electrode includes a partially insulated wire, which serves as the support structure, and wherein non-insulated portions of the wire serve as respective ones of the intra-pulposus exposed electrode surfaces.

Inventive concept 70. The apparatus according to any one of inventive concepts 57-62, wherein the apparatus includes at least one intra-pulposus electrode, which includes:
- at least two of the intra-pulposus exposed electrode surfaces; and
- a support structure along which the at least two of the intra-pulposus exposed electrode surfaces are disposed, wherein the support structure is configured to remain straight during and after implantation.

Inventive concept 71. The apparatus according to inventive concept 70, wherein the at least one intra-pulposus electrode includes a partially insulated wire, which serves as the support structure, and wherein non-insulated portions of the wire serve as respective ones of the intra-pulposus exposed electrode surfaces.

Inventive concept 72. The apparatus according to inventive concept 70,
- wherein the at least two of the intra-pulposus exposed electrode surfaces include first, second, and third intra-pulposus exposed electrode surfaces disposed along the support structure, with the second longitudinally between the first and the third intra-pulposus exposed electrode surfaces, and
- wherein the control circuitry is configured to configure the first, the second, and the third intra-pulposus exposed electrode surfaces to be at respective different potentials, the potential at the second intra-pulposus exposed electrode surface (a) greater than the potential at the first intra-pulposus exposed electrode surface, and (b) greater than the potential at the third intra-pulposus exposed electrode surface.

Inventive concept 73. The apparatus according to any one of inventive concepts 57-62, wherein the apparatus includes at least one intra-pulposus electrode, which includes:
- at least two of the intra-pulposus exposed electrode surfaces; and
- a support structure, which includes a plurality of spines that respectively include one or more of the intra-pulposus exposed electrode surfaces.

Inventive concept 74. The apparatus according to inventive concept 73, wherein the support structure further includes a backbone, from which the spines extend.

Inventive concept 75. The apparatus according to inventive concept 73, wherein the support structure includes a partially insulated wire, and wherein non-insulated portions of the wire serve as respective ones of the intra-pulposus exposed electrode surfaces.

There is additionally provided, in accordance with an inventive concept 76 of the present invention, apparatus for treating an intervertebral disc of a subject, the apparatus including:
- one or more intra-pulposus exposed electrode surfaces;
- a support structure along which the one or more intra-pulposus exposed electrode surfaces are disposed, wherein the support structure is configured to be implanted within a nucleus pulposus of the disc, and to be shaped as a partial ring or a complete ring after implantation;
- one or more extra-pulposus exposed electrode surfaces, which are configured to be implanted outside the nucleus pulposus, in electrical communication with the disc; and
- control circuitry, which is configured to:
  - configure the intra-pulposus exposed electrode surfaces to be cathodes, and the one or more extra-pulposus exposed electrode surfaces to be one or more anodes, and
  - drive the intra-pulposus exposed electrode surfaces and the one or more extra-pulposus exposed electrode surfaces to electroosmotically drive fluid into the nucleus pulposus.

Inventive concept 77. The apparatus according to inventive concept 76, wherein the support structure includes a wire, and wherein the one or more intra-pulposus exposed electrode surfaces are defined by one or more non-insulated portions of the wire.

Inventive concept 78. The apparatus according to inventive concept 77, wherein the wire has a diameter of no more than 200 microns.

Inventive concept 79. The apparatus according to inventive concept 76, wherein the support structure is configured to be shaped as the complete ring that surrounds an area of at least 1 cm2 upon implantation.

Inventive concept 80. The apparatus according to inventive concept 76, wherein the support structure is configured to be shaped as the partial ring that surrounds an area of at least 1 cm2 upon implantation.

There is additionally provided, in accordance with an inventive concept 81 of the present invention, a method including:
- systemically administering a drug to a blood circulation of a subject; and
- activating control circuitry to apply, using one or more implanted electrodes, a current that drives the administered drug from the blood circulation into tissue of the subject, including at at least one point in time at which the drug has a concentration in the blood circulation equal to at least 75% of a maximum concentration of the drug in the blood circulation.

Inventive concept 82. The method according to inventive concept 81 wherein driving the administered drug includes ceasing to drive the administered drug within an amount of time after or before the concentration drops below a percentage of the maximum concentration, the amount of time between 15 and 60 minutes, and the percentage between 5% and 20%.

Inventive concept 83. The method according to inventive concept 81, wherein driving the administered drug includes ceasing to drive the administered drug only after the concentration drops below 40% of the maximum concentration.

Inventive concept 84. The method according to inventive concept 81, wherein driving includes beginning driving the administered drug within 5 minutes before or after beginning systemically administering the drug.

Inventive concept 85. The method according to inventive concept 84, wherein driving includes beginning driving the administered drug within 1 minute before or after beginning systemically administering the drug.

Inventive concept 86. The method according to inventive concept 81, wherein driving includes beginning driving the administered drug within 5 minutes before or after beginning systemically administering the drug.

Inventive concept 87. The method according to inventive concept 81, wherein driving includes beginning driving the administered drug within a certain amount of time before or after beginning systemically administering the drug, the certain amount of time based on predetermined pharmacokinetics of the drug.

Inventive concept 88. The method according to inventive concept 81, wherein driving includes beginning driving the administered drug within 5 minutes before or after the concentration of the drug in the blood circulation first exceeds 25% of the maximum concentration of the drug in the blood circulation.

Inventive concept 89. The method according to inventive concept 81, wherein driving the drug includes providing a user-activation input to the control circuitry, and wherein the control circuitry is configured to begin driving the drug after a delay from receiving the user-activation input.

Inventive concept 90. The method according to inventive concept 89, wherein the delay is based on predetermined pharmacokinetics of the drug.

Inventive concept 91. The method according to inventive concept 81, wherein the one or more electrodes are implanted in the subject within 2 cm of the tissue.

Inventive concept 92. The method according to inventive concept 81, wherein the one or more electrodes are implanted in the subject within 1 cm of the tissue.

Inventive concept 93. The method according to inventive concept 81, wherein driving includes driving the administered drug for an amount of time based on predetermined pharmacokinetics of the drug.

Inventive concept 94. The method according to inventive concept 81, wherein driving the drug includes driving the drug from the blood circulation into an intervertebral disc of the subject.

Inventive concept 95. The method according to inventive concept 81, wherein driving the drug includes driving the drug from the blood circulation into a kidney of the subject.

Inventive concept 96. The method according to inventive concept 81, wherein driving the drug includes driving the drug from the blood circulation into cartilage of the subject.

Inventive concept 97. The method according to inventive concept 81, wherein driving the drug includes driving the drug from the blood circulation into brain tissue of the subject.

Inventive concept 98. The method according to inventive concept 97, wherein at least a first one of the electrodes is implanted in a cerebral blood vessel, and at least a second one of the electrodes is implanted in the brain tissue.

Inventive concept 99. The method according to inventive concept 81, wherein systemically administering the drug includes parenterally administering the drug.

Inventive concept 100. The method according to inventive concept 99, wherein systemically administering the drug includes injecting the drug to an intracorporeal site of the subject within 10 cm of the tissue.

Inventive concept 101. The method according to inventive concept 81, wherein systemically administering the drug includes enterally administering the drug.

Inventive concept 102. The method according to inventive concept 81, wherein systemically administering the drug includes implanting a drug reservoir containing the drug.

Inventive concept 103. The method according to inventive concept 81, wherein systemically administering the drug includes transdermally administering the drug.

Inventive concept 104. The method according to inventive concept 103, wherein transdermally administering the drug includes driving the drug through skin of the subject.

Inventive concept 105. The method according to inventive concept 81, wherein systemically administering the drug includes systemically administering the drug using an administration device that is configured, upon administering the drug, to activate the control circuitry to apply the current.

Inventive concept 106. The method according to inventive concept 105, wherein the administration device includes a syringe, and wherein systemically administering the drug includes systemically administering the drug using the syringe.

There is also provided, in accordance with an inventive concept 107 of the present invention, a method including:
administering a drug to a subject; and
driving the administered drug into target tissue of the subject, by activating electrodes that were implanted in a body of the subject at least one day before administering the drug, at least one of the electrodes disposed within 2 cm of target tissue of the subject.

Inventive concept 108. The method according to inventive concept 107, wherein administering the drug includes administering the drug to an intracorporeal site of the subject within 10 cm of the target tissue.

Inventive concept 109. The method according to inventive concept 107, wherein the at least one of the electrodes is disposed within 1 cm of the target tissue.

There is further provided, in accordance with an inventive concept of the present invention, a method including:
implanting electrodes in a body of a subject, such that at least one of the electrodes is disposed within 2 cm of target tissue of the subject;
implanting, in the body of the subject, control circuitry configured to drive the electrodes to apply an iontophoretic current configured to drive a drug into the target tissue; and
not implanting a drug reservoir containing the drug disposed for delivery by the iontophoretic current.

Inventive concept 111. The method according to inventive concept 110, wherein implanting the electrodes includes implanting the electrodes such that the at least one of the electrodes is disposed within 1 cm of the target tissue.

The present invention will be more fully understood from the following detailed description of embodiments thereof, taken together with the drawings, in which:

BRIEF DESCRIPTION OF THE DRAWINGS

FIGS. 1A-C are schematic illustrations of a system for treating an intervertebral disc of a subject, in accordance with respective applications of the present invention;

FIGS. 2A-C are schematic illustrations of additional configurations of the system of FIGS. 1A-C, in accordance with respective applications of the present invention.

DETAILED DESCRIPTION OF APPLICATIONS

Figure 1B:
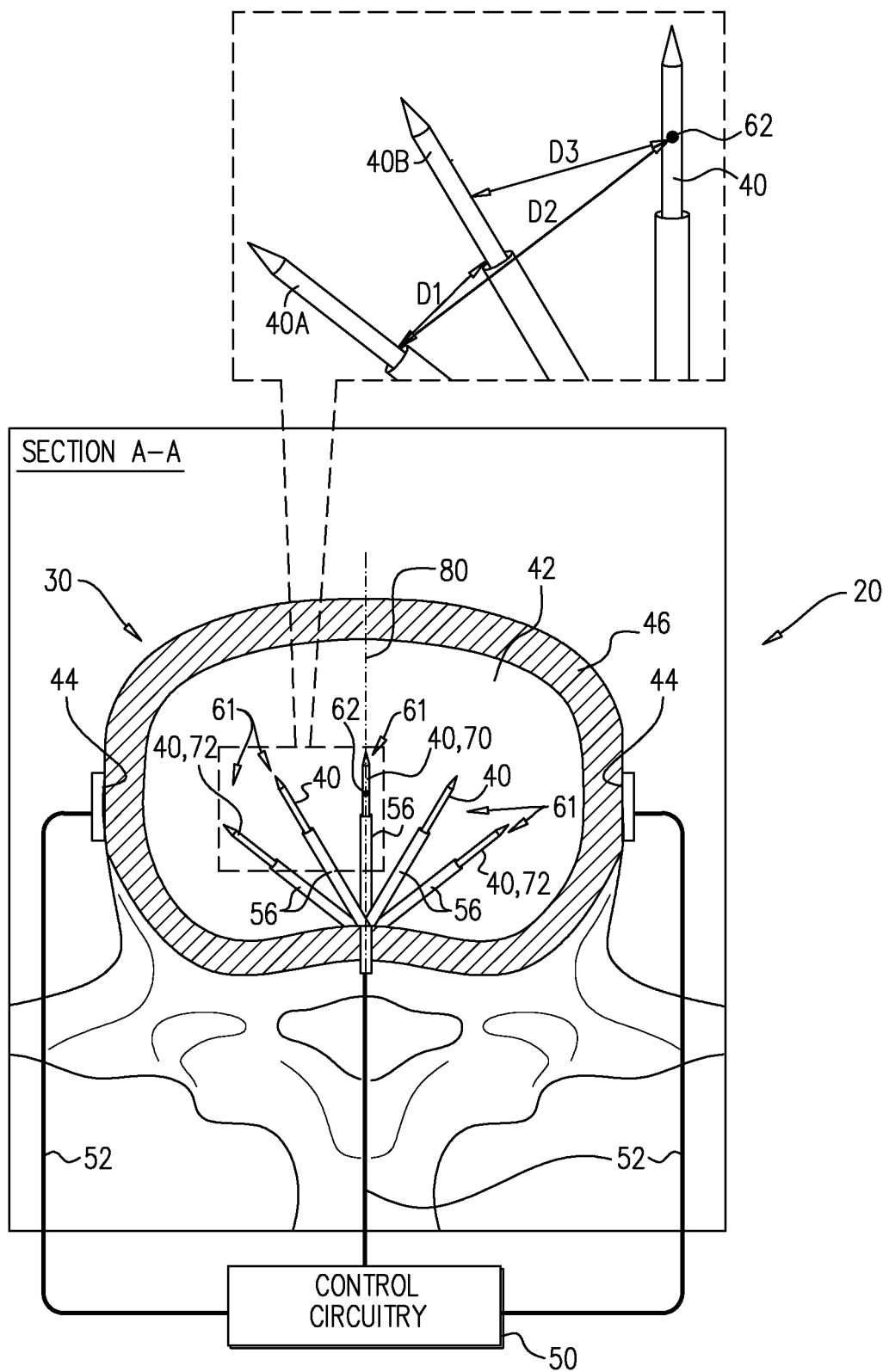
Figure 1C:
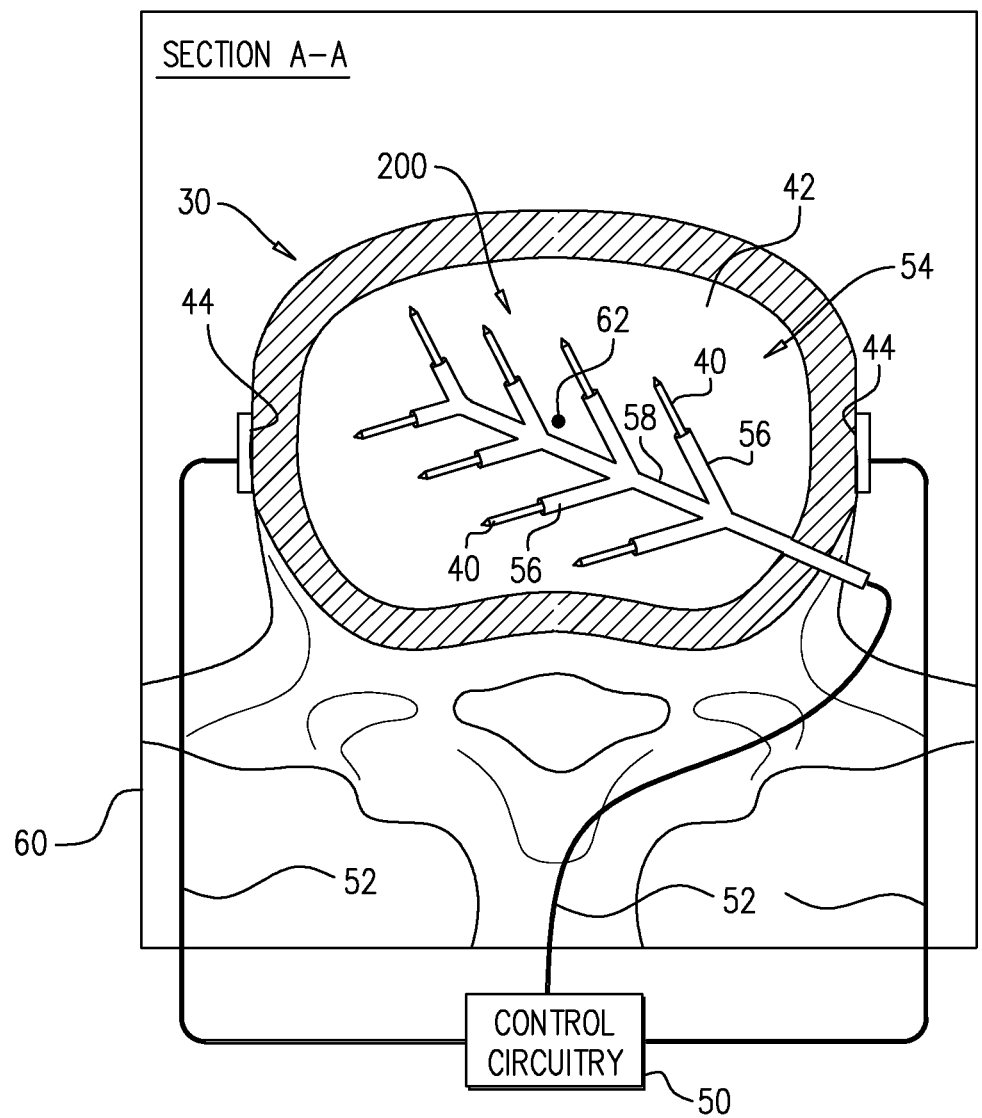

FIGS. 1A-C are schematic illustrations of a system 20 for treating an intervertebral disc 30 of a subject, in accordance with respective applications of the present invention. System 20 comprises (a) at least two (typically, at least three) intra-pulposus exposed electrode surfaces 40, which are electrically conductive, and which are configured to be implanted (typically chronically) within a nucleus pulposus 42 of disc 30 at different respective locations, and (b) one or more extra-pulposus exposed electrode surfaces 44, which are configured to be implanted (typically chronically) outside nucleus pulposus 42, in electrical communication with disc 30, in a vicinity of an external surface of an annulus fibrosus 46 of disc 30, e.g., in physical contact with the external surface. Alternatively, second electrode 32 is configured to be at least partially inserted into annulus fibrosus 46 (configuration not shown). System 20 further comprises implantable (typically chronically implantable) or external control circuitry 50, which is typically coupled to the exposed electrode surfaces by one or more electrode leads 52. For some applications, control circuitry 50 is configured to control each of the exposed electrode surfaces separately; for example, control circuitry 50 may be electrically coupled to the exposed electrode surfaces separately via separate electrical conductors.

For some applications, the electrodes are implanted during a conventional surgical procedure to repair disc 30 and/or nucleus pulposus 42, including a standard approach for inserting a needle in disc 30.

For some applications system 20 comprises at least one intra-pulposus electrode, which comprises a support structure 54 which comprises or is shaped so as to define intra-pulposus exposed electrode surfaces 40. For some applications, support structure 54 comprises a shape memory alloy, such as Nitinol, which is configured to automatically assume a predetermined shape when in a relaxed state upon implantation in the disc.

Reference is made to FIGS. 1B and 1C. For some applications, support structure 54 comprises a plurality of spines 56 that respectively comprise one or more (e.g., exactly one) of intra-pulposus exposed electrode surfaces 40. For some applications, spines 56 assume their respective angular positions upon initial insertion through annulus fibrosus 46 and into nucleus pulposus 42, and then are advanced in respective paths farther into nucleus pulposus 42. Alternatively, spines 56 are advanced toward a geometric center 62 of disc 30 while constrained in an introducer tube (e.g., a hollow needle), and, upon release from the introducer tube, radially separate from one another until spines 56 assume their respective angular positions. For some applications, such as shown in FIG. 1C, support structure 54 further comprises a backbone 58, from which spines 56 extend. For some applications, the intra-pulposus electrode is implanted such that backbone 58 remains straight during and after the implanting.

For some applications, such as of the configurations shown in FIGS. 1B and 1C, support structure 54 comprises a partially insulated wire, and non-insulated portions of the wire serve as respective ones of intra-pulposus exposed electrode surfaces 40. For some applications, the wire has a diameter of at least 10 microns, such as at least 20 microns, and no more than 200 microns, such as no more than 100 microns, no more than 50 microns, or no more than 10 microns. Such a fine electrode generally avoids any potential damage to the disc. For some applications, the electrode is introduced within an introducer, which may, for example, have an outer diameter of between 100 and 300 microns, e.g., between 100 and 200 microns.

For some applications, intra-pulposus exposed electrode surfaces 40 are shaped to have a relatively large surface area. For example, intra-pulposus exposed electrode surfaces 40 may be shaped as blades rather than cylinders. Large surface areas allow application of greater current at any given voltage. In general, in these applications it is desired for the voltage to not exceed 1.2 V, in order to minimize the risk of causing electrolysis of at least one of the electrode surfaces.

In some applications of the present invention, a method of treating intervertebral disc 30 comprises implanting, within nucleus pulposus 42 of disc 30, the at least two (typically at least three, e.g., at least four, at least five, at least six, at least seven, or more than seven) intra-pulposus exposed electrode surfaces 40 at different respective locations. The method further comprises implanting the one or more extra-pulposus exposed electrode surfaces 44 outside nucleus pulposus 42, in electrical communication with disc 30.

After the intra-pulposus exposed electrode surfaces 40 and the one or more extra-pulposus exposed electrode surfaces 44 have been implanted, control circuitry 50 is activated to drive the intra-pulposus exposed electrode surfaces 40 and the one or more extra-pulposus exposed electrode surfaces 44 to electroosmotically drive fluid between inside and outside nucleus pulposus 42.

Typically, a healthcare worker, such as a physician, activates control circuitry 50 to provide the functions described herein. Activating the control circuitry may include configuring parameters and/or functions of the control circuitry (such as using a separate programmer or external controller), or activating the control circuitry to perform functions pre-programmed in the control circuitry. Control circuitry 50 typically comprises appropriate memory, processor(s), and hardware running software that is configured to provide the functionality of the control circuitry described herein.

For some applications, the intra-pulposus exposed electrode surfaces 40 are implanted such that if intra-pulposus exposed electrode surfaces 40 were to be projected onto a transverse plane 60 of disc 30, the intra-pulposus exposed electrode surfaces 40 would be at different respective projected locations 61 in transverse plane 60. It is noted that intra-pulposus exposed electrode surfaces 40 may be implanted at different respective heights within disc 30 (i.e., axial positions along the vertebral column), i.e., intra-pulposus exposed electrode surfaces 40 may or may not be implanted in transverse plane 60. The projection of intra-pulposus exposed electrode surfaces 40 onto transverse plane 60 described and claimed in the present application is not a physical step of the implantation method, but is instead a geometric way of describing the relative positions of the electrode surfaces.

For some applications, intra-pulposus exposed electrode surfaces 40 are implanted such that if intra-pulposus exposed electrode surfaces 40 were to be projected onto transverse plane 60, each of intra-pulposus exposed electrode surfaces 40 would be at least 2 mm from a closest another one of the intra-pulposus exposed electrode surfaces 40, such as at least 3 mm, e.g., at least 5 mm, as measured between closest respective points of the two intra-pulposus exposed electrode surfaces 40. For example, in the blow-ups in FIGS. 1A and 1B, a first intra-pulposus exposed electrode surface 40A is at a distance D1 from a closest second intra-pulposus exposed electrode surface 40B.

For some applications, intra-pulposus exposed electrode surfaces 40 are implanted such that if intra-pulposus exposed electrode surfaces 40 were to be projected onto transverse plane 60, at least two of intra-pulposus exposed electrode surfaces 40 would be disposed at respective different distances from geometric center 62 of disc 30 in transverse plane 60, as measured between closest respective points of the at least two of intra-pulposus exposed electrode surfaces 40 and geometric center 62. For example, in the blow-up in FIGS. 1A and 1B, first intra-pulposus exposed electrode surface 40A is at a distance D2 from geometric center 62, and second intra-pulposus exposed electrode surface 40B is at a distance D3 from geometric center 62.

For some applications, intra-pulposus exposed electrode surfaces 40 are implanted such that if intra-pulposus exposed electrode surfaces 40 were to be projected onto transverse plane 60, at least three of intra-pulposus exposed electrode surfaces 40 would be disposed at respective different distances from geometric center 62 of disc 30 in transverse plane 60, as measured between closest respective points of the at least three of intra-pulposus exposed electrode surfaces 40 and geometric center 62. Alternatively or additionally, for some applications, intra-pulposus exposed electrode surfaces 40 are implanted such that if intra-pulposus exposed electrode surfaces 40 were to be projected onto transverse plane 60, at least one of the distances would be at least 2 mm greater than another one of the distances, such as at least 3 mm greater, e.g., at least 5 mm greater.

Further alternatively or additionally, for some applications, intra-pulposus exposed electrode surfaces 40 are implanted such that if intra-pulposus exposed electrode surfaces 40 were to be projected onto transverse plane 60, at least (a) a first one of the distances from geometric center 62 would be at least 2 mm greater than a second one of the distances from geometric center 62 (e.g., at least 3 mm greater, such as at least 5 mm greater), and (b) a third one of one of the distances from geometric center 62 would be at least 2 mm greater than the second one of the distances from geometric center 62 (e.g., at least 3 mm greater, such as at least 5 mm greater).

Alternatively or additionally, for some applications, the intra-pulposus exposed electrode surfaces 40 are implanted such that a smallest one of the distances from geometric center 62 is no more than 5 mm, such as no more than 3 mm, e.g., no more than 2 mm, such as no more than 1 mm. Still further alternatively or additionally, for some applications, intra-pulposus exposed electrode surfaces 40 are implanted such that if intra-pulposus exposed electrode surfaces 40 were to be projected onto transverse plane 60, at least one of intra-pulposus exposed electrode surfaces 40 would be disposed at a distance of no more than 10 mm, such as no more than 5 mm, from a geometric center of disc 30 in transverse plane 60, as measured between a closest point of the intra-pulposus exposed electrode surface 40 and geometric center 62.

As used in the present application, including in the claims, geometric center 62 (also known in the mathematical arts as the centroid) is the arithmetic mean ("average") position of all the points in disc 30 (including both nucleus pulposus 42 and annulus fibrosus 46). As used in the present application, including in the claims, a transverse plane (also called the horizontal plane, axial plane, or transaxial plane) is an imaginary plane that divides the body into superior and inferior parts, and is perpendicular to the coronal and sagittal planes.

For some applications, as shown in FIGS. 1A and 1B, intra-pulposus exposed electrode surfaces 40 are implanted symmetrically about a sagittal plane 80 of disc 30 (i.e., with reflection symmetry).

For some applications, control circuitry 50 is configured to drive intra-pulposus exposed electrode surfaces 40 and the one or more extra-pulposus exposed electrode surfaces 44 to electroosmotically drive fluid between inside and outside nucleus pulposus 42 by applying (a) a first voltage between at least a first one of intra-pulposus exposed electrode surfaces 40 and at least one of the one or more extra-pulposus exposed electrode surfaces 44, and (b) a second voltage between at least a second one of intra-pulposus exposed electrode surfaces 40 and at least one of the one or more extra-pulposus exposed electrode surfaces 44, the second voltage different from the first voltage. For some of these applications, control circuitry 50 is configured to drive intra-pulposus exposed electrode surfaces 40 and the one or more extra-pulposus exposed electrode surfaces 44 to electroosmotically drive fluid between inside and outside nucleus pulposus 42 by applying a third voltage between at least a third one of intra-pulposus exposed electrode surfaces 40 and at least one of the one or more extra-pulposus exposed electrode surfaces 44, the third voltage different from at least one of the first and the second voltages, such as different from both the first and the second voltages. For example, control circuitry 50 may be configured to separately drive respective currents between intra-pulposus exposed electrode surfaces 40 and the one or more extra-pulposus exposed electrode surface 44.

For some applications, control circuitry 50 is activated to configure the current to increase pressure in disc 30 by electroosmotically driving the fluid into nucleus pulposus 42. Such an increase in fluid in nucleus pulposus 42 generally treats or prevents further degeneration of the disc caused at least in part by loss of fluid. Typically, in these applications, control circuitry 50 is activated to configure the intra-pulposus exposed electrode surfaces 40 to be cathodes, and the one or more extra-pulposus exposed electrode surface 44 to be one or more anodes. The applied current may also help introduce nutritional substances into the disc.

For some of these applications, control circuitry 50 is configured to configure the cathodes to be at different respective negative potentials (typically, by separately controlling each of the cathodes). For some of these applications, if the cathodes were to be projected onto transverse plane 60, one or more of the cathodes would be one or more respective closest cathodes 70 to geometric center 62 of disc 30 in transverse plane 60, as measured between closest respective points of the cathodes and geometric center 62 of disc 30. Control circuitry 50 is configured to set respective magnitudes of the negative potentials at the one or more closest cathodes 70 to be at least 30 mV with respect to outside nucleus pulposus 42, such as at least 40 mV with respect to outside nucleus pulposus 42. Alternatively or additionally, for some of these applications, if the cathodes were to be projected onto transverse plane 60, one or more of the cathodes would be one or more respective farthest cathodes 72 from geometric center 62 of disc 30 in transverse plane 60, and control circuitry 50 is configured to set respective magnitudes of the negative potentials at the one or more farthest cathodes 72 to be no more than 20 mV with respect to outside nucleus pulposus 42.

For some applications, control circuitry 50 is configured to set respective magnitudes of the negative potentials at the cathodes, with respect to outside nucleus pulposus 42, to be inversely related to respective distances between geometric center 62 and the cathodes. For some of these applications, if the cathodes were to be projected onto transverse plane 60, one or more of the cathodes would be one or more respective closest cathodes 70 to geometric center 62 of disc 30 in transverse plane 60, and one or more of the cathodes would be one or more respective farthest cathodes 72 to geometric center 62 of disc 30 in transverse plane 60. Control circuitry 50 is configured to set respective magnitudes of the negative potentials at the one or more closest cathodes 70, with respect to outside nucleus pulposus 42, to be greater than respective magnitudes of the negative potential at the one or more farthest cathodes 72, with respect to outside nucleus pulposus 42. For some applications, control circuitry 50 is configured to set the respective magnitudes of the negative potentials at the one or more closest cathodes 70, with respect to outside nucleus pulposus 42, to be at least 20 mV greater than (e.g., at least 30 mV greater than) the respective magnitudes of the negative potentials at the one or more farthest cathodes 72, with respect to outside nucleus pulposus 42, and/or to be no more than 1.2 V (e.g., no more than 70 mV) greater than the respective magnitudes of the negative potentials at the one or more farthest cathodes 72, with respect to outside nucleus pulposus 42.

For some applications, intra-pulposus exposed electrode surfaces 40 are configured to apply respective currents, such that at least two of the currents are different from each other, even though the same voltage is applied. For example, intra-pulposus exposed electrode surfaces 40 may be coated with slightly-insulating coatings, with at least two of the coatings having differing thicknesses. Alternatively, at least two of intra-pulposus exposed electrode surfaces 40 may have different lengths or surface areas.

For some applications, control circuitry 50 is activated to configure the current to reduce pressure in disc 30 by electroosmotically driving the fluid from nucleus pulposus 42, such as in order to treat disc herniation. For an example, one or more intra-pulposus exposed electrode surfaces 40 may be positioned close to the zone of the herniation, and one or more extra-pulposus exposed electrode surfaces 44 may be positioned immediately outside the herniation. For example, an electrode mount (e.g., shaped like a two-headed rivet) may be provided that is shaped so as to cross annulus fibrosus 46 and hold the intra-pulposus and extra-pulposus exposed electrode surfaces 40 and 42 in place. Typically, in these applications, control circuitry 50 is activated to configure intra-pulposus exposed electrode surfaces 40 to be anodes, and the one or more extra-pulposus exposed electrode surfaces 44 to be one or more cathodes. These applications may implement any of the techniques and parameters described herein for applications in which intra-pulposus exposed electrode surfaces 40 are configured to be cathodes, with the reverse polarity.

For some applications, control circuitry 50 is activated to apply a voltage of up to 1.2 V, for example, between 200 and 500 mV, between intra-pulposus exposed electrode surfaces 40 and the one or more extra-pulposus exposed electrode surface 44. (Typically, the natural voltage across the outer membrane of disc 30 is about 50-70 mV.) For some applications, control circuitry 50 is activated to apply the current with a low frequency, such as between 0.5 and 2 Hz. This frequency is typically insufficient to stimulate a nerve, which typically requires about 5-20 Hz. Alternatively or additionally, the duty cycle is typically low, e.g., less than 40%. Typically, control circuitry 50 is activated to apply the current monophasically, in order to drive the fluid in only one direction. In contrast, nerve stimulators typically apply a few volts, and do not cause electrolysis because the applied signal is biphasic.

Figure 2A:
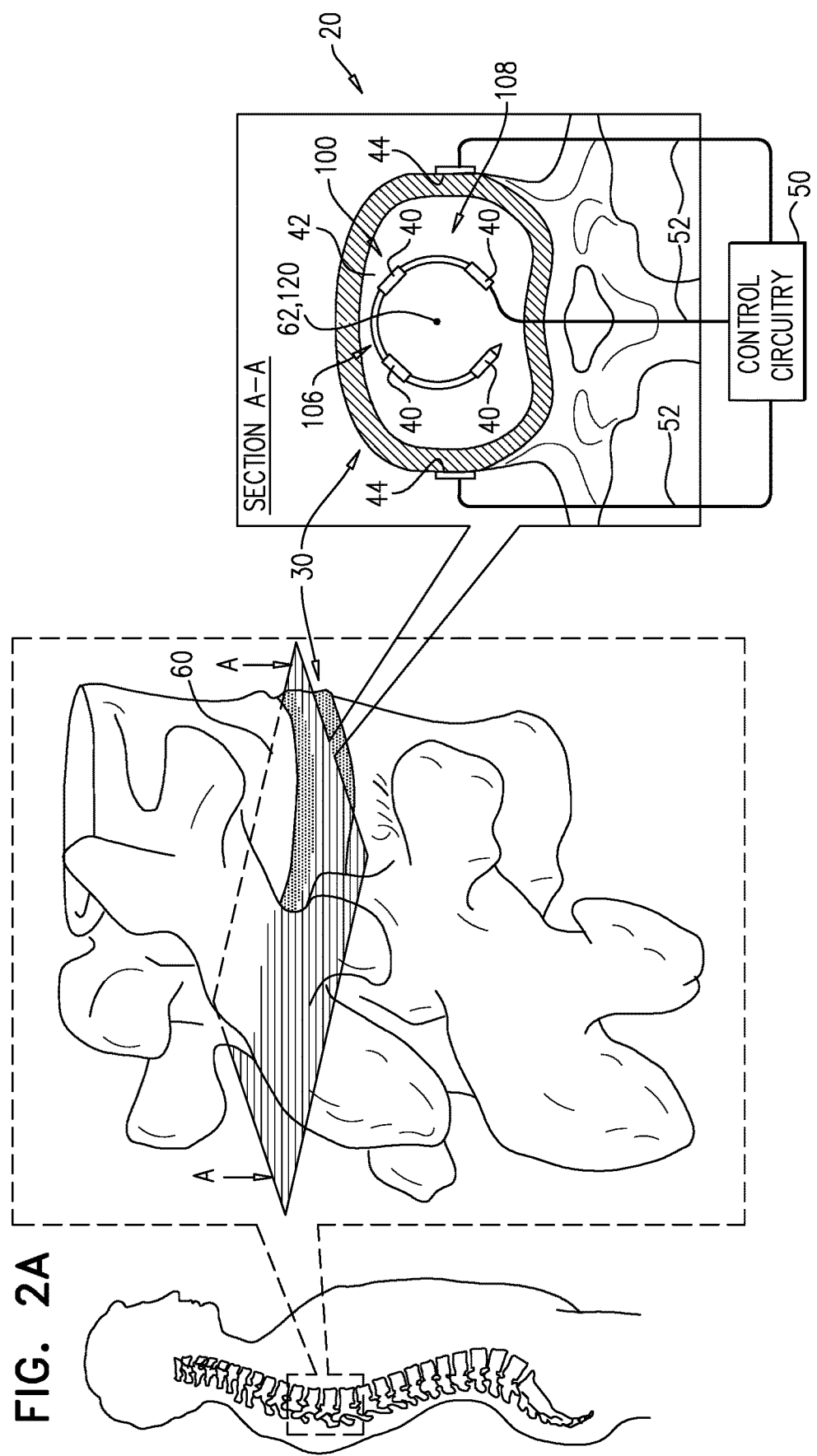
Figure 2B:
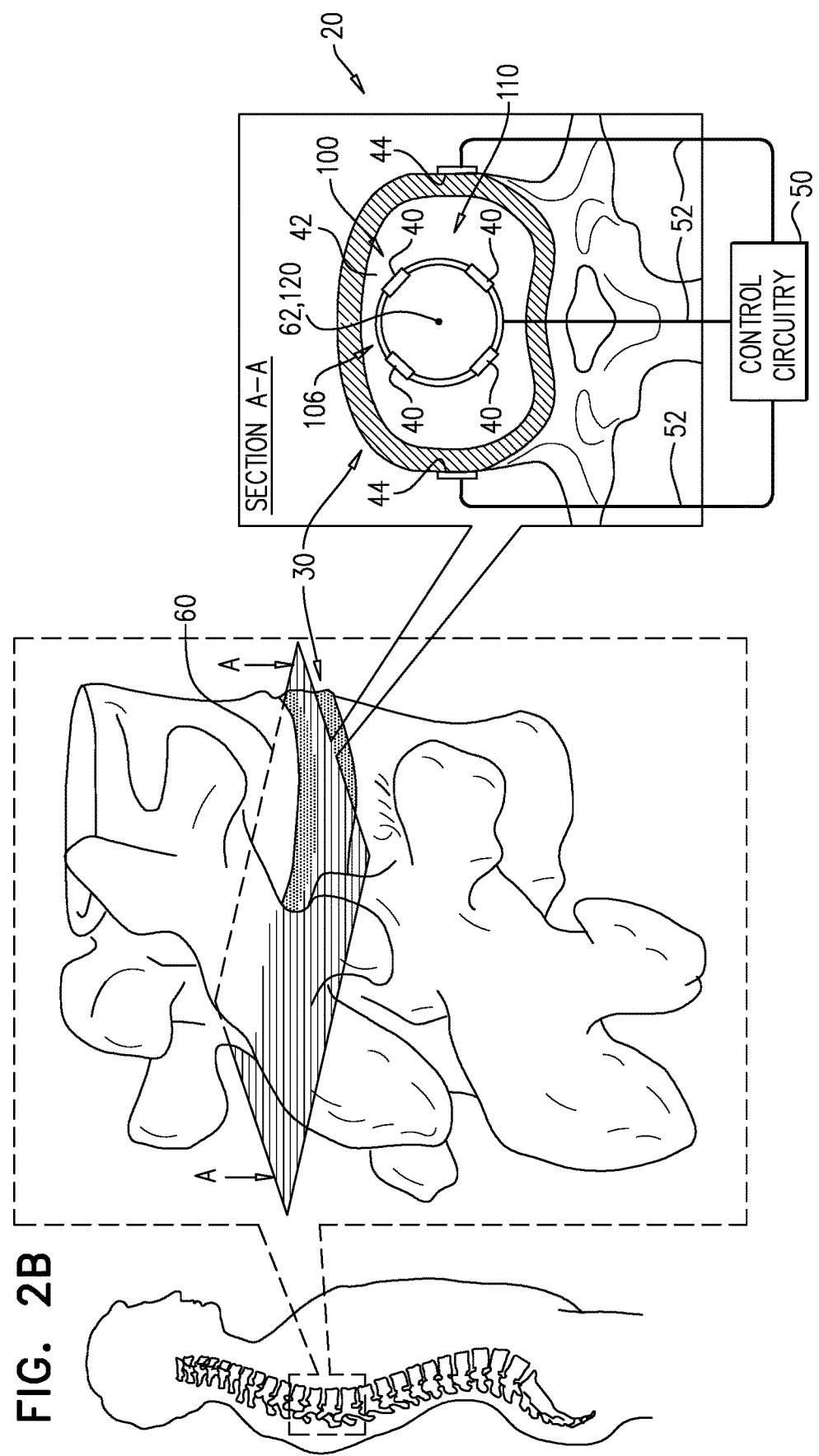

Reference is now made to FIGS. 2A-C, which are schematic illustrations of additional configurations of system 20, in accordance with respective applications of the present invention. In the configurations shown in FIGS. 2A-B, implanting intra-pulposus exposed electrode surfaces 40 comprises implanting at least one intra-pulposus electrode 100, which comprises (a) at least two of intra-pulposus exposed electrode surfaces 40, and (b) a support structure 106 along which the at least two of intra-pulposus exposed electrode surfaces 40 are disposed, such that support structure 106 is shaped as a partial ring 108 (as shown in FIG. 2A) or a complete ring 110 (as shown in FIG. 2B) after the implanting. For some applications, support structure 106 comprises a shape memory alloy, such as Nitinol, which is configured to automatically assume the partial or complete ring shape when in a relaxed state upon implantation in the disc. For some applications, the intra-pulposus electrode 100 is implanted from the angular approach shown in FIG. 2C.

Disc 30 defines a geometric center line segment 120 perpendicular to transverse plane 60 of disc 30. For some applications, the at least one intra-pulposus electrode 100 is implanted such that support structure 106 surrounds at least 180 degrees of geometric center line segment 120, such as at least 210 degrees, at least 240 degrees, at least 270 degrees, at least 300 degrees, at least 330 degrees, or 360 degrees (as shown in FIG. 2B).

For some applications, such as shown in FIG. 2A, the at least one intra-pulposus electrode 100 is implanted such that the support structure is shaped as partial ring 108 that surrounds an area of at least 1 cm2, such as at least 1.5 cm2 or at least 2 cm2 and/or an area equal to at least 15%, such as at least 20% or at least 25%, of a greatest area of nucleus pulposus 42 measured in a transverse plane of disc 30. For some applications, partial ring 108 has a length, measured along support structure 106, of at least 1.5 cm (e.g., at least 2 cm), no more than 6 cm (e.g., no more than 4 cm), and/or between 1.5 cm (e.g., 2 cm) and 6 cm (e.g., 4 cm).

For some applications, such as shown in FIG. 2B, the at least one intra-pulposus electrode 100 is implanted such that support structure 106 is shaped as complete ring 110 that surrounds an area of at least 1 cm2, such at least 1.5 cm2 or at least 2 cm2 and/or an area equal to at least 15%, such as at least 20% or at least 25%, of a greatest area of nucleus pulposus 42 measured in a transverse plane of disc 30. For some applications, complete ring 110 has a perimeter of at least 1.5 cm (e.g., at least 2 cm), no more than 6 cm (e.g., no more than 4 cm), and/or between 1.5 cm (e.g., 2 cm) and 6 cm (e.g., 4 cm).

For some applications, such as of the configurations shown in FIGS. 2A and 2B, support structure 106 is shaped and intra-pulposus exposed electrode surfaces 40 are disposed on support structure 106 such that, upon implantation, intra-pulposus exposed electrode surfaces 40 are approximately equidistant from geometric center line segment 120, i.e., (a) a first distance between center line segment 120 and a first one of the intra-pulposus exposed electrode surfaces 40 farthest from center line segment 120 is no more than 120%, e.g., 110%, of (a) a second distance between center line segment 120 and a second one of the intra-pulposus exposed electrode surfaces 40 closest to center line segment 120.

For some applications, such as of the configurations shown in FIGS. 2A and 2B, the at least one intra-pulposus electrode 100 comprises a partially insulated wire, which serves as support structure 106, and non-insulated portions of the wire serve as respective ones of intra-pulposus exposed electrode surfaces 40. For some applications, the wire has a diameter of at least 10 microns, such as at least 20 microns, and no more than 200 microns, such as no more than 100 microns, no more than 50 microns, or no more than 10 microns. Such a fine electrode generally avoids any potential damage to the disc. For some applications, the electrode is introduced within an introducer, which may, for example, have an outer diameter of between 100 and 300 microns, e.g., between 100 and 200 microns.

For some applications, the configurations shown in FIGS. 2A and 2B are instead implemented using a single, long intra-pulposus exposed electrode surface 40. For some applications, the single intra-pulposus exposed electrode surface 40 has a perimeter of at least 1.5 cm (e.g., at least 2 cm), no more than 6 cm (e.g., no more than 4 cm), and/or between 1.5 cm (e.g., 2 cm) and 6 cm (e.g., 4 cm).

In the configuration shown in FIG. 2C, implanting intra-pulposus exposed electrode surfaces 40 comprises implanting at least one intra-pulposus electrode 200, which comprises: (a) at least two of intra-pulposus exposed electrode surfaces 40, and (b) a support structure 222 along which the at least two of intra-pulposus exposed electrode surfaces 40 are disposed, such that support structure 222 remains straight during and after the implanting. For some applications, intra-pulposus exposed electrode surfaces 40 are implanted such that if intra-pulposus exposed electrode surfaces 40 were to be projected onto transverse plane 60, a closest one of intra-pulposus exposed electrode surfaces 40 would be disposed within 10 mm, such as 5 mm, of geometric center 62 of disc 30 in transverse plane 60, as measured between a closest point of the intra-pulposus exposed electrode surface and geometric center 62. For some applications, support structure 222 comprises a shape memory alloy, such as Nitinol.

For some applications, the at least two of intra-pulposus exposed electrode surfaces 40 include first, second, and third intra-pulposus exposed electrode surfaces 40A, 40B, and 40C disposed along support structure 222, with second intra-pulposus exposed electrode surface 40B longitudinally between first and third intra-pulposus exposed electrode surfaces 40A and 40C. Control circuitry 50 is activated to configure first, second, and third intra-pulposus exposed electrode surfaces 40A, 40B, and 40C to be at respective negative potentials (e.g., negative potentials), the potential (e.g., negative potential) at second intra-pulposus exposed electrode surface 40B (a) greater than the potential (e.g., negative potential) at first intra-pulposus exposed electrode surface 40A, and (b) greater than the potential (e.g., negative potential) at third intra-pulposus exposed electrode surface 40C. For some applications, the potential (e.g., negative potential) at first intra-pulposus exposed electrode surface 40A is equal to the potential (e.g., negative potential) at third intra-pulposus exposed electrode surface 40C.

For some applications, intra-pulposus exposed electrode surfaces 40 are implanted such that if intra-pulposus exposed electrode surfaces 40 were to be projected onto transverse plane 60: (a) first, second, and third intra-pulposus exposed electrode surfaces 40A, 40B, and 40C would be disposed at respective first, second, and third distances from geometric center 62 in transverse plane 60, as measured between closest respective points of the intra-pulposus exposed electrode surfaces and geometric center 62, and (b) the second distance would be (a) less than the first distance, and (b) less than the third distance. For some applications, the first distance equals the second distance.

Although intra-pulposus electrode 200 is shown in FIG. 2C as comprising three intra-pulposus exposed electrode surfaces 40, intra-pulposus electrode 200 may alternatively comprise more intra-pulposus exposed electrode surfaces 40, such as 4, 5, 6, 7, 8, or 9 intra-pulposus exposed electrode surfaces 40. For example, intra-pulposus electrode 200 may comprise 7 intra-pulposus exposed electrode surfaces 40, and control circuitry 50 may be activated to configure the negative potentials at intra-pulposus exposed electrode surfaces 40 to be −30 mV, −40 mV, −45 mV, −50 mV, −45 mV, −40 mV, and −30 mV, respectively, with respect to outside the nucleus pulposus.

Reference is made to FIGS. 1A-2C. For some applications, the one or more extra-pulposus exposed electrode surfaces 44 are implanted within 1 mm of nucleus pulposus 42 of disc 30, or between 1 and 15 mm, such as between 1 and 5 mm, from nucleus pulposus 42 of disc 30. For some applications, the one or more extra-pulposus exposed electrode surfaces 44 are implanted within 1 mm of the external surface of annulus fibrosus 46, such as in contact with the external surface. Alternatively or additionally, for some applications, the one or more extra-pulposus exposed electrode surfaces 44 are implanted at least partially within annulus fibrosus 46 of disc 30.

For some applications, the more extra-pulposus exposed electrode surfaces 44 provided, the closer the extra-pulposus exposed electrode surfaces are implanted to nucleus pulposus 42, in order to generate a generally uniform flow of current from the electrode surfaces within the disc to outside of the disc. If instead only a single extra-pulposus exposed electrode surface 44 were provided and it were positioned near or touching the disc, a distorted field distribution would result. However, if the single extra-pulposus exposed electrode surface 44 is disposed farther from the disc, a more uniform field results because current flows somewhat equally between the single extra-pulposus exposed electrode surface 44 and each of the intra-pulposus exposed electrode surfaces 40. Nevertheless, the inventors have identified that it would be desirable not to place extra-pulposus exposed electrode surface 44 so far from the disc that the voltage required to maintain a sufficient current would exceed about 1.2 V, because this would have a risk of causing electrolysis of at least one of the electrode surfaces. Correspondingly, if more intra-pulposus exposed electrode surfaces 40 are provided, they may be disposed closer to the disc and still result in a generally uniform field distribution. For some applications, in light of the above considerations, two to four (e.g., three) extra-pulposus exposed electrode surfaces 44 are used, and are disposed within 2, 3, or 4 cm of the disc, but greater than 1 cm from the disc.

For some applications, the one or more extra-pulposus exposed electrode surfaces 44 are implanted at an average distance from nucleus pulposus 42 that is inversely related to a number of the one or more extra-pulposus exposed electrode surfaces 44 being implanted. For example, the one or more extra-pulposus exposed electrode surfaces 44 may be implanted such that a product of (a) the number of the one or more extra-pulposus exposed electrode surfaces 44 times (b) the average distance in centimeters of the one or more extra-pulposus exposed electrode surfaces 44 from the nucleus pulposus equals between 4 and 15.

For some applications, control circuitry 50 is configured to apply direct current, e.g., with an average amplitude of between 1 and 5 mA. For some applications, the control unit is configured to apply the direct current with an average amplitude of less than 1.2 V. For some applications, the control unit is configured to apply the direct current as a series of pulses. For some applications, the control unit is configured to apply the direct current as the series of pulses with a duty cycle of between 1% and 50%.

Reference is still made to FIGS. 1A-2C. For some applications, control circuit is configured to:
  drive intra-pulposus exposed electrode surfaces 40 and the one or more extra-pulposus exposed electrode surfaces 44 to electroosmotically drive fluid between inside and outside nucleus pulposus 42 during a plurality of discrete activation periods alternating with non-activation periods, and
  ramp a strength of currents applied between intra-pulposus exposed electrode surfaces 40 and the one or more extra-pulposus exposed electrode surfaces 44 at a beginning of at least one of the activation periods such that the strength reaches a maximum value no earlier than 10 minutes after the beginning of the period, such as no earlier than 15 minutes after the beginning of the period.

Such a slow ramp-up in the strength may simulate natural physiology, rather provide a step function. For some applications, control circuitry 50 is configured to set a length of at least one of the non-activation periods to be at least 30 minutes.

For some applications, control circuitry 50 is configured to drive intra-pulposus exposed electrode surfaces 40 and the one or more extra-pulposus exposed electrode surfaces 44 to electroosmotically drive fluid between inside and outside nucleus pulposus 42 based on a circadian cycle of the subject.

Reference is still made to FIGS. 1A-2C. For some applications, a housing containing control circuitry is injectable, with an anchor at the proximal end. One or more extra-pulposus exposed electrode surfaces 44 are fixed to an external surface of the housing. For example, the housing may be implanted immediately posterior to the spinal column.

Reference is still made to FIGS. 1A-2C. For some applications, control circuitry 50 is configured to be implanted subcutaneously, if the housing containing the control circuitry is small. Alternatively, for some applications, control circuitry 50 is configured to be implanted or elsewhere in the subject's body, if the housing of the control circuitry is larger (e.g., includes batteries).

For some applications, control circuitry 50 is driven by an external controller that is in wireless or wired communication with control circuitry 50. For some applications, the external controller is mounted on a bed of the subject (e.g., disposed within a mattress), and is configured to activate control circuitry 50 only at night, and/or only when the subject is sleeping. Such nighttime activation may coincide with and support the filling phase of the disc, and thus be therapeutic even though the patient experiences more pain during the day. Alternatively or additionally, control circuitry 50 is activated during the daytime, i.e., over the course of the day, because the pressure is higher in the disc during application of vertical and mechanical load on the disc, which causes the disc to lose fluid; the activation may this reduce maximum damage to the disc. Further alternatively, the control circuitry is activated generally constantly, or regularly intermittently (e.g., one hour on/one hour off. For some applications, control circuitry 50 is activated during rest of the subject, rather than during activity; for example, an accelerometer may be provided to identify movement vs. rest of the subject.

For some applications, control circuitry 50 is configured to provide the subject with control of activation of control circuitry 50, e.g., in response to activity or pain. For example, the control may be provided from the subject's telephone (e.g., smartphone) or other electronic device.

For some applications, the method further comprises replacing nucleus pulposus 42 with an artificial substitute material before implanting intra-pulposus exposed electrode surfaces 40.

A first experiment was conducted on behalf of the inventors to study the feasibility of using some of the techniques described hereinabove with reference to FIGS. 1A-2C to hydrate and dehydrate a spinal disc, and the impact of the voltage application on the disc mass. The experiment evaluated three electrical protocols: (a) negative voltage inside the nucleus pulposus of the disc vs. outside the disc, (b) positive voltage inside the nucleus pulposus of the disc vs. outside the disc, and (c) control (no voltage applied to the nucleus pulposus of the disc). It was found that application of a negative voltage inside the nucleus pulposus of the disc enhanced the hydration of the disc, as compared to a positive voltage or no voltage. No dehydration effect was observed with application of a positive voltage to the nucleus pulposus.

The experiment used a total of six fresh bovine tail discs. In order to achieve equilibrium, the discs were placed in a saline solution for a period of one hour prior to application of the voltages. The discs were then weighed. The discs were randomly assigned to the experimental groups as follows: (a) two specimens—negative voltage inside the nucleus pulposus of the disc vs. outside the disc, (b) two specimens—positive voltage inside the nucleus pulposus of the disc vs. outside the disc, and (c) two specimens—control (no voltage applied to the nucleus pulposus of the disc).

The discs were placed inside a vessel and fully submerged in saline solution. One electrode was inserted in the approximate center of the nucleus pulposus of each of the discs in experimental groups (a) and (b). The electrode was electrically-insulated except at its tip, and was designed to allow submersion in liquid. The electrode was inserted laterally (i.e., through the annulus of the disc). A second, ring electrode was placed within the saline solution surrounding the disc.

Voltages of (a) −1 V and (b) +1 V were applied between the electrodes in the two experimental groups (a) and (b), respectively. These voltages were selected to be lower than the electrolysis voltage of water of about 1.2 V. After a period of two hours, the discs were removed and weighed again.

As set forth in Table 1 below, all of the discs increased in mass during the voltage-application period. The mass of the discs to which the negative internal voltage was applied increased by 4.7% and 5.5%, while the mass of the other discs (positive internal voltage and control) increased by between 2.0% and 2.6%.

The inventors hypothesize that all of the discs absorbed liquid, while the application of the negative internal voltage contributed to an additional absorption of 2-3%. The application of the positive internal voltage did not result in dehydration of the disc.

TABLE 1

| Disc # | Mass after 1 hour immersion [g] | Voltage (internal) | Mass after 2 hours voltage application [g] | Mass change [g] | Mass change [%] |
| --- | --- | --- | --- | --- | --- |
| 1 | 3.342 | −1 V | 3.527 | 0.185 | 5.5% |
| 2 | 4.384 | −1 V | 4.590 | 0.206 | 4.7% |
| 3 | 6.552 | +1 V | 6.720 | 0.168 | 2.6% |
| 4 | 4.558 | +1 V | 4.651 | 0.093 | 2.0% |
| 5 | 7.346 | 0 | 7.531 | 0.185 | 2.5% |
| 6 | 6.074 | 0 | 6.209 | 0.135 | 2.2% |

A second experiment was conducted on behalf of the inventors to study the feasibility of using some of the techniques described hereinabove with reference to FIGS. 1A-2C to hydrate a spinal disc and the impact of the voltage application on the disc mass. The experiment evaluated two electrical protocols: (a) negative voltage inside the nucleus pulposus of the disc vs. outside the disc, and (b) control (no voltage applied to the nucleus pulposus of the disc). It was found that application of a negative voltage inside the nucleus pulposus of the disc enhanced the hydration of the disc, as compared to no voltage. Higher voltage markedly increased the mass gain.

The experiment used a total of six fresh bovine tail discs. The discs were randomly assigned to the experimental groups as follows: (a) three specimens—negative voltage inside the nucleus pulposus of the disc vs. outside the disc, and (b) three specimens—control (no voltage applied to the nucleus pulposus of the disc).

The discs were weighed, and then placed inside a vessel and fully submerged in saline solution. One electrode was inserted in the approximate center of the nucleus pulposus of each of the discs in the experimental group (a). The electrode was electrically-insulated except at its tip, and was designed to allow submersion in liquid. The electrode was inserted laterally (i.e., through the annulus of the disc). A second, ring electrode was placed within the saline solution surrounding the disc.

A voltage of −1 V was applied between the electrodes in the experimental group (a). One hour after the beginning of application of the voltage, a first pair of two of the discs (one negative voltage, one control) were removed and weighed. In the two remaining negative voltage discs, the voltage was increased to −3 V.

Two hours after the beginning of application of the voltage, a second pair of two of the discs (one negative voltage, one control) were removed and weighed.

Three hours after the beginning of application of the voltage, a third pair of two of the discs (one negative voltage, one control) were removed and weighed.

As set forth in Table 2 below, all of the discs increased in mass during the voltage-application period. In each pair, the disc to which the voltage was applied increased in mass more than the control disc did. Increasing the voltage from −1 V to −3 V resulted in a markedly increased mass gain. It was noted, however, that the −3 V voltage application resulted in electrolysis of the solution, which was expected since the electrolysis threshold of water is about 1.2 V. This electrolysis was observed as bubbles and discoloration in the solution.

The inventors hypothesize that all of the discs absorbed liquid, while the application of the negative internal voltage contributed to an additional absorption.

TABLE 2

| Disc # | Starting mass [g] | Voltage (internal) | Duration of voltage application | Ending mass [g] | Mass change [%] |
|---|---|---|---|---|---|
| 1 | 6.047 | −1 V | 1 hour | 6.345 | 4.93% |
| 2 | 6.227 | 0 | 1 hour | 6.420 | 3.10% |
| 3 | 5.988 | −1 V, −3 V | 2 hours | 6.605 | 10.30% |
| 4 | 5.192 | 0 | 2 hours | 5.444 | 4.85% |
| 5 | 4.484 | −1 V, −3 V | 3 hours | 5.262 | 17.35% |
| 6 | 4.236 | 0 | 3 hours | 4.619 | 9.04% |

The inventors hypothesize that application of −3 V, although possibly not suitable for clinical use, served as a proxy for the effectiveness of longer-term voltage application at a lower voltage, such as −1 V.

As mentioned above, the discs were placed in a saline-dye solution during the experiment. The dye was methylene blue. After weighing the discs, the discs were also dissected and inspected for dye penetration. In general, dye penetration was not observed in the discs.

Figure 3:
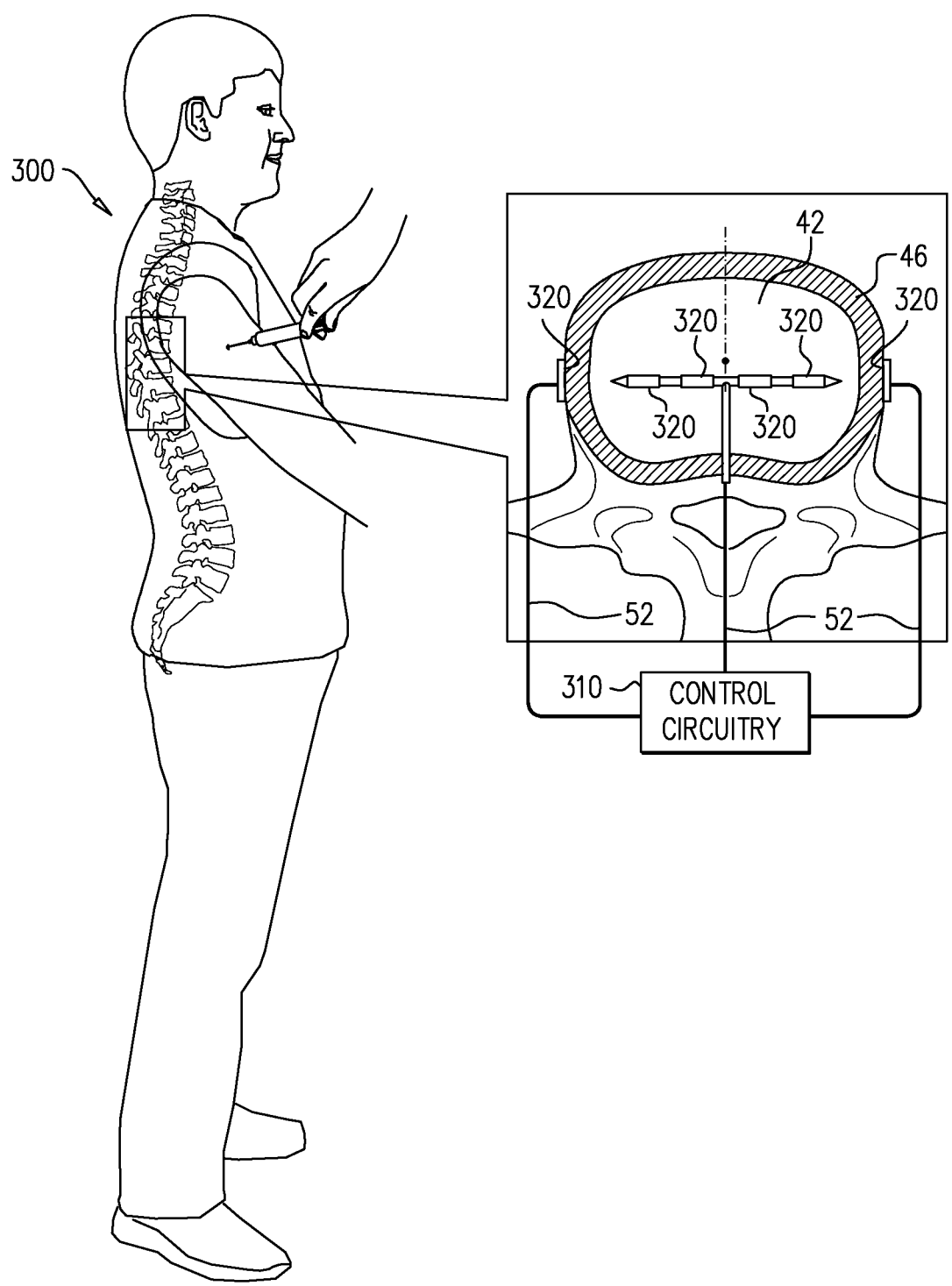
FIG. 3 is a schematic illustration of a method of administering a drug, in accordance with an application of the present invention.

Reference is now made to FIG. 3, which is a schematic illustration of a method of administering a drug, in accordance with an application of the present invention. The method comprises systemically administering the drug to a blood circulation of a subject 300, and activating control circuitry 310 to apply, using one or more implanted electrodes 320, a current that drives the administered drug from the blood circulation into tissue of subject 300, including at at least one point in time at which the drug has a concentration in the blood circulation equal to at least 75% of a maximum concentration of the drug in the blood circulation. For example, the current may drive the drug into the tissue iontophoretically and/or electroosmotically (e.g., fluid may be driven into the tissue electroosmotically, and the drug may be driven into the tissue iontophoretically). The drug typically is water-soluble, and has an effective polarity and/or net electric charge once dissolved in water. For some applications, control circuitry 310 and/or implanted electrodes 320 are implemented using techniques described hereinabove with reference to FIGS. 1A-C, 2A, 2B, and/or 2C, mutatis mutandis.

As used in the present application, including in the claims, systemic administration means the administration of a drug into the circulatory system so that the entire body is affected, and may occur via enteral administration or parenteral administration (e.g., injection, infusion, or implantation).

For some applications, driving the administered drug comprises ceasing drive the administered drug within an amount of time after or before the concentration drops below a percentage of the maximum concentration, the amount of time between 15 and 60 minutes, and the percentage between 5% and 20%.

For some applications, driving the administered drug comprises ceasing to drive the administered drug only after the concentration drops below 40% of the maximum concentration.

For some applications, driving comprises beginning driving the administered drug within 5 minutes before or after beginning systemically administering the drug. For some applications, driving comprises beginning driving the administered drug within 1 minute before or after beginning systemically administering the drug., such as within 5 seconds before or after beginning systemically administering the drug, e.g., simultaneously with beginning systemically administering the drug.

For some applications, driving comprises beginning driving the administered drug within 5 minutes before or after beginning systemically administering the drug.

For some applications, driving comprises beginning driving the administered drug within a certain amount of time before or after beginning systemically administering the drug, the certain amount of time based on predetermined pharmacokinetics of the drug. For some applications, driving comprises driving the administered drug for an amount of time based on predetermined pharmacokinetics of the drug. For example, the predetermined pharmacokinetics of the drug may be determined based on studies (pharmacokenetics), rather than personally for the subject; alternatively, the predetermined pharmacokinetics of the drug may be determined personally for the patient, such as using a sensor.

For some applications, driving comprises beginning driving the administered drug within 5 minutes before or after the concentration of the drug in the blood circulation first exceeds 25% of the maximum concentration of the drug in the blood circulation.

For some applications, driving the drug comprises providing a user-activation input to control circuitry 310, and control circuitry 310 is configured to begin driving the drug after a delay from receiving the user-activation input. For some applications, the delay is based on predetermined pharmacokinetics of the drug.

For some applications, the one or more electrodes 320 are implanted in the subject within 2 cm of the tissue, such 1 cm of the tissue, e.g., with 0.5 cm of the tissue.

For some applications, driving the drug comprises driving the drug from the blood circulation into intervertebral disc 30 of the subject (as shown in FIG. 3), a kidney of the subject, an eye of the subject, or cartilage of the subject, such as cartilage of the knee.

For other applications, driving the drug comprises driving the drug from the blood circulation into brain tissue of the subject (across the blood-brain barrier). For example, at least a first one of electrodes 320 may be implanted in a cerebral blood vessel (e.g., a vein), and at least a second one of electrodes 320 may be implanted in the brain tissue), for example, control circuitry 310 may configure the first one of electrodes 320 to have a negative potential, and the second one of electrodes 320 to have a positive potential. For example, the drug may be administered to treat Alzheimer's disease.

More generally, the drug may be driven across any membrane in the body.

For some applications, systemically administering the drug comprises parenterally administering the drug, such as by injection or infusion. For some applications, systemically administering the drug comprises injecting the drug to an intracorporeal site of the subject within 10 cm of the tissue (i.e., the administration apparatus (e.g., needle) is positioned at the intracorporeal site, not that the drug eventually arrives at the intracorporeal site). For other applications, systemically administering the drug comprises enterally (e.g., orally or sublingually) administering the drug. Alternatively, systemically administering the drug comprises implanting a drug reservoir containing the drug. Alternatively, systemically administering the drug comprises transdermally administering the drug, such as by driving the drug through skin of the subject.

For some applications, the drug is systemically administered using an administration device that is configured, upon administering the drug, to activate control circuitry 310 to apply the current. For some applications, the administration device comprises a syringe, and systemically administering the drug comprises systemically administering the drug using the syringe.

Reference is still made to FIG. 3. In some applications of the present invention, a method is provided that comprises administering a drug to subject 300, and driving the administered drug into target tissue of the subject, by activating electrodes 320 that were implanted in a body of the subject at least one day before administering the drug, at least one of the electrodes disposed within 2 cm of target tissue of the subject.

For some applications, administering the drug comprises administering the drug to an intracorporeal site of the subject within 2 cm of the target tissue. For some applications, the at least one of the electrodes is disposed within 1 cm of the target tissue, such as within 0.5 cm of the target tissue.

Reference is still made to FIG. 3. In some applications of the present invention, a method is provided that comprises:
  implanting electrodes 320 in a body of subject 300, such that at least one of electrodes 320 is disposed within 2 cm of target tissue of the subject;
  implanting, in the body of subject 300, control circuitry 310 configured to drive electrodes 320 to apply an iontophoretic current configured to drive a drug into the target tissue; and
  not implanting a drug reservoir containing the drug disposed for delivery by the iontophoretic current.

For some applications, implanting electrodes 320 comprises implanting electrodes 320 such that the at least one of the electrodes 320 is disposed within 1 cm of the target tissue, such as within 0.5 cm of the target tissue.

In some applications of the present invention, the techniques and apparatus described herein are combined with techniques and apparatus described in one or more of the following applications, which are assigned to the assignee of the present application and are incorporated herein by reference:
  U.S. Pat. No. 8,577,469 to Gross; and
  U.S. Patent Application Publication 2014/0324128 to Gross.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating an intervertebral disc of a subject, the apparatus comprising:
  one or more intra-pulposus exposed electrode surfaces;
  a support structure along which the one or more intra-pulposus exposed electrode surfaces are disposed, wherein the support structure is configured to be implanted within a nucleus pulposus of the disc, and to be shaped as a partial ring or a complete ring after implantation;
  one or more extra-pulposus exposed electrode surfaces, which are configured to be implanted outside the nucleus pulposus, in electrical communication with the disc; and
  control circuitry, which is configured to:
    configure the intra-pulposus exposed electrode surfaces to be cathodes, and the one or more extra-pulposus exposed electrode surfaces to be one or more anodes, and
    drive the intra-pulposus exposed electrode surfaces and the one or more extra-pulposus exposed electrode surfaces to electroosmotically drive fluid into the nucleus pulposus.

2. The apparatus according to claim 1, wherein the support structure comprises a wire, and wherein the one or more intra-pulposus exposed electrode surfaces are defined by one or more non-insulated portions of the wire.

3. The apparatus according to claim 2, wherein the wire has a diameter of no more than 200 microns.

4. The apparatus according to claim 1, wherein the support structure is configured to be shaped as the complete ring that surrounds an area of at least 1 cm2 upon implantation.

5. The apparatus according to claim 1, wherein the support structure is configured to be shaped as the partial ring that surrounds an area of at least 1 cm2 upon implantation.

6. The apparatus according to claim 1, wherein the one or more intra-pulposus exposed electrode surfaces comprise at least two intra-pulposus exposed electrode surfaces, which are disposed along the support structure.

7. A method of treating an intervertebral disc of a subject, comprising:
  implanting, within a nucleus pulposus of the disc, a support structure along which one or more intra-pulposus exposed electrode surfaces are disposed, such that the support structure is shaped as a partial ring or a complete ring after the implanting;

implanting one or more extra-pulposus exposed electrode surfaces outside the nucleus pulposus, in electrical communication with the disc; and activating control circuitry to:

configure the intra-pulposus exposed electrode surfaces to be cathodes, and the one or more extra-pulposus exposed electrode surfaces to be one or more anodes, and, drive the intra-pulposus exposed electrode surfaces and the one or more extra-pulposus exposed electrode surfaces to electroosmotically drive fluid into the nucleus pulposus to increase pressure in the disc.

8. The method according to claim 7, wherein the support structure includes a wire, and wherein the one or more intra-pulposus exposed electrode surfaces are defined by one or more non-insulated portions of the wire.

9. The method according to claim 8, wherein the wire has a diameter of no more than 200 microns.

10. The method according to claim 7,
wherein the disc defines a geometric center line segment perpendicular to a transverse plane of the disc, and
wherein implanting the support structure comprises implanting the support structure such that the support structure surrounds at least 180 degrees of the geometric center line segment.

11. The method according to claim 10, wherein implanting the support structure comprises implanting the support structure such that the support structure surrounds at least 270 degrees of the geometric center line segment.

12. The method according to claim 7, wherein implanting the support structure comprises implanting the support structure such that the support structure is shaped as the complete ring that surrounds an area of at least 1 cm2.

13. The method according to claim 7, wherein implanting the support structure comprises implanting the support structure such that the support structure is shaped as the complete ring that surrounds an area equal to at least 15% of a greatest area of the nucleus pulposus measured in a transverse plane of the disc.

14. The method according to claim 7, wherein implanting the support structure comprises implanting the support structure such that the support structure is shaped as the partial ring that surrounds an area of at least 1 cm2.

15. The method according to claim 7, wherein implanting the support structure comprises implanting the support structure such that the support structure is shaped as the partial ring that surrounds an area equal to at least 15% of a greatest area of the nucleus pulposus measured in a transverse plane of the disc.

16. The method according to claim 7, wherein the one or more intra-pulposus exposed electrode surfaces include at least two intra-pulposus exposed electrode surfaces, which are disposed along the support structure.

* * * * *